US011247001B2

(12) United States Patent
O'Flaherty et al.

(10) Patent No.: US 11,247,001 B2
(45) Date of Patent: Feb. 15, 2022

(54) DELIVERY DEVICE WITH CANTILEVER STRUCTURE AND ASSOCIATED METHOD OF USE

(71) Applicant: De Motu Cordis Pty Ltd, Wilston (AU)

(72) Inventors: Brendan O'Flaherty, Wilston (AU); Johann Lipman, Wilston (AU); John Fraser, Wilston (AU); Shaun Gregory, Wilston (AU)

(73) Assignee: De Motu Cordis Pty Ltd, Wilston (AU)

( * ) Notice: Subject to any disclaimer, the term of this patent is extended or adjusted under 35 U.S.C. 154(b) by 382 days.

(21) Appl. No.: 16/338,311

(22) PCT Filed: Sep. 29, 2017

(86) PCT No.: PCT/AU2017/051073
§ 371 (c)(1),
(2) Date: Mar. 29, 2019

(87) PCT Pub. No.: WO2018/058201
PCT Pub. Date: Apr. 5, 2018

(65) Prior Publication Data
US 2020/0023147 A1    Jan. 23, 2020

(30) Foreign Application Priority Data

Sep. 30, 2016 (AU) ................................ 2016903990

(51) Int. Cl.
*A61M 15/00* (2006.01)
(52) U.S. Cl.
CPC .... *A61M 15/0005* (2014.02); *A61M 15/0013* (2014.02); *A61M 15/0018* (2014.02);
(Continued)

(58) Field of Classification Search
CPC .......... A61M 15/0005; A61M 15/0041; A61M 15/0013; A61M 15/0018; A61M 15/0045
See application file for complete search history.

(56) References Cited

U.S. PATENT DOCUMENTS 4,452,239 A * 6/1984 Malem ............... A61M 15/0086
128/200.17
4,706,663 A * 11/1987 Makiej .................. A61M 15/00
128/200.18
(Continued)

FOREIGN PATENT DOCUMENTS

EP          0729762       9/1996
WO      WO 98/04308      2/1998
(Continued)

*Primary Examiner* — Kathryn E Ditmer
(74) *Attorney, Agent, or Firm* — Womble Bond Dickinson (US) LLP

(57) ABSTRACT

A delivery device for use in administering a dry powder to a biological subject's airway is provided. The device comprises (a) a housing having an inlet in fluid communication with an outlet for delivering a flow of gas to the subject's airway; and (b) one or more cantilever structures located within the housing. Vibration of the one or more cantilever structures facilitates entry of the dry powder into the flow of gas, such that the dry powder can be delivered by the flow of gas through the outlet to the subject's airway. Also provided is a container for releasably storing a particulate composition, the container comprising a shell sealed by a seal in which the particulate composition is stored, wherein a puncturing device for rupturing the seal to release the particulate composition is housed within the shell. Further provided are associated methods for administering dry powder using the delivery device and/or container.

12 Claims, 35 Drawing Sheets

(52) U.S. Cl.
CPC .... *A61M 15/0031* (2014.02); *A61M 15/0045* (2013.01); *A61M 15/0021* (2014.02); *A61M 15/0041* (2014.02); *A61M 2202/0007* (2013.01); *A61M 2202/064* (2013.01); *A61M 2205/43* (2013.01); *A61M 2206/20* (2013.01)

(56) References Cited

U.S. PATENT DOCUMENTS

| | | | | |
|---|---|---|---|---|
| 4,976,259 | A * | 12/1990 | Higson | A61M 15/0085 128/200.14 |
| 4,981,368 | A * | 1/1991 | Smith | B01F 5/0473 366/337 |
| 5,676,130 | A * | 10/1997 | Gupte | A61M 15/0086 128/203.19 |
| 5,724,959 | A * | 3/1998 | McAughey | A61M 15/00 128/203.15 |
| 6,318,360 | B1 | 11/2001 | Attolini | |
| 2002/0088462 | A1 * | 7/2002 | Genova | A61M 11/005 128/203.15 |
| 2003/0047620 | A1 * | 3/2003 | Litherland | A61M 15/0085 239/102.1 |
| 2007/0221218 | A1 | 9/2007 | Warden et al. | |
| 2008/0127671 | A1 * | 6/2008 | Kim | F24F 1/0007 62/467 |
| 2009/0134235 | A1 * | 5/2009 | Ivri | H01L 41/053 239/4 |
| 2010/0051023 | A1 * | 3/2010 | Kladders | A61M 15/0028 128/200.21 |
| 2010/0139655 | A1 * | 6/2010 | Genosar | A61M 15/001 128/203.15 |
| 2012/0234322 | A1 * | 9/2012 | Smyth | A61M 15/0038 128/203.15 |
| 2013/0032145 | A1 * | 2/2013 | Adler | A61M 15/0008 128/203.15 |
| 2014/0083423 | A1 * | 3/2014 | Jung | A61M 15/0028 128/203.21 |
| 2015/0107589 | A1 * | 4/2015 | Longest | A61M 15/003 128/203.15 |
| 2015/0190594 | A1 * | 7/2015 | Elmaleh | A61M 15/0035 128/203.15 |
| 2016/0213866 | A1 * | 7/2016 | Tan | A61M 11/042 |

FOREIGN PATENT DOCUMENTS

| | | |
|---|---|---|
| WO | WO 2015/085362 | 6/2015 |
| WO | WO 2016/055655 | 4/2016 |

* cited by examiner

SECTION A-A

SECTION A-A

SECTION A-A

```
Generate flow of gas between inlet
and outlet of delivery device              1500
                │
                ▼
Release particulate medicament
within device housing and entrain          1510
medicament in gas flow
                │
                ▼
Deliver particulate medicament to          1530
subject's airway
```

Figure 15

| Material | Specific Modulus (E/ρ, m^2/s^2) |
|---|---|
| General Purpose Polystyrene (GPPS) | 3.15 |
| Polyurethane 1 (ECC PU) | 2.27 |
| ECC PU w/ 8%VV Talc | 2.23 |
| Polyurethane 2 (TC808) | 1.36 |

| Product | Inspiratory Flow Rate at 4kPa Pressure Drop (L/min) | Inspiratory Resistance (kPa ^0.5. min/L) |
|---|---|---|
| Breezhaler | 111 | 0.017 |
| Aerolizer | 102 | 0.019 |
| ELLIPTA | 74 | 0.027 |
| Novolizer | 72 | 0.027 |
| Accuhaler | 72 | 0.027 |
| CURRENT DEVICE | 70 | 0.029 |
| Genuair | 64 | 0.031 |
| TurbohalerSymbicort | 58 | 0.035 |
| NEXThaler | 54 | 0.036 |
| TurbohalerPulmicort | 54 | 0.039 |
| Twisthaler | 47 | 0.044 |
| Easyhaler | 41 | 0.050 |
| Handihaler | 37 | 0.058 |

Figure 25

DELIVERY DEVICE WITH CANTILEVER STRUCTURE AND ASSOCIATED METHOD OF USE

CROSS-REFERENCE TO RELATED APPLICATIONS

This application is a national stage filing under 35 U.S.C. 371 of PCT/AU2017/051073, filed Sep. 29, 2017, which International Application was published by the International Bureau in English on Apr. 5, 2018, and this application claims priority from Australian Application No. 2016903990, filed on Sep. 30, 2016, which applications are hereby incorporated in their entirety by reference in this application.

BACKGROUND OF THE INVENTION

The present invention relates to a delivery device for use in administering a particulate medicament or dry powder to a biological subject's airway, and to an associated method of use. The invention also relates to a container for storing particulate compositions, such as dry powders.

DESCRIPTION OF THE PRIOR ART

The reference in this specification to any prior publication (or information derived from it), or to any matter which is known, is not, and should not be taken as an acknowledgment or admission or any form of suggestion that the prior publication (or information derived from it) or known matter forms part of the common general knowledge in the field of endeavour to which this specification relates.

Cardiac arrest is a significant cause of mortality, with as many as 500,000 deaths reported in the USA each year and almost 90% of cases occurring at home or in the community. Survivors frequently have devastating brain injury due to the variable period of brain hypoxia suffered. Current data shows survival post cardiac arrest is 24-40% in hospital vs. 9% survival in community. "Survival" is not an acceptable outcome—it must be useful survival. The difference is largely attributable to delays in return of cerebral perfusion. Unlike most other organs, the brain has minimal metabolic reserve or ability to generate energy anaerobically, and thus irreversible damage commences within seconds of cardiac arrest. It is estimated that if new strategies could reduce cardiac arrest mortality by 10%, this would reduce the cost incurred through cardiac arrests by $75 billion.

It is known to administer drugs such as adrenaline (also known as epinephrine) and atropine to subjects in cardiac arrest, and in particular during cardiopulmonary resuscitation (CPR).

Conventional CPR is a known technique which involves performing chest compressions on, and supplying artificial breaths (also known as rescue breaths) to, the subject. In this regard, the Australian Resuscitation Council recommends that CPR be performed using a 30:2 compression to ventilation ratio with minimal interruptions. The Council further recommends that 1 mg of adrenaline be administered to subjects with a shockable heart rhythm after every second shock and every two CPR loops thereafter. For subjects with non-shockable heart rhythms, it is recommended that 1 mg of adrenaline be administered immediately and every two CPR loops thereafter. However, these doses could be subject to variation. The use of adrenaline during CPR is also recommended in guidelines published by various resuscitation councils and societies around the world as can be found for instance at www.ilcor.org/home.

It is known that CPR temporarily maintains blood flow to the brain thus preserving brain function while medical treatment is sought. The additional administration of adrenaline is known to improve return of spontaneous circulation, strengthen cardiac contractions, increase macrocirculatory pressure, and thus increase survival rates, and in particular increase post-resuscitation quality of life of subjects, for example, by decreasing the risk of severe permanent disability post-resuscitation.

However delivery of adrenaline typically involves either intravenous injection, or administering a dose of liquid adrenaline into the subject's trachea. In this regard, if a single operator is performing CPR on a subject, it will be necessary to interrupt the compressions and ventilation in order to administer the adrenaline which is contrary to the best practices outlined above, and can adversely affect the subject. In addition, the administration of adrenaline using any of the abovementioned methods requires considerable medical training, and therefore typically cannot be performed in circumstances where trained medical personnel are not present, severely impacting the subject's chances for recovery and a higher quality of life post-resuscitation. Both methods also have a number of further disadvantages.

The former method requires access to a vein in order to inject the adrenaline, which can be particularly problematic for subjects with heart dysfunction, where veins are difficult to access due to little or no blood circulation. In the event it is possible to access a vein, the lack of circulation also prevents any injected adrenaline from travelling to the cardiac tissue, and as a result it is typically necessary to further administer intravenous saline in order to encourage circulation of the drug. Furthermore, it can be particularly difficult to gain access to a vein if the subject is a child or infant.

The latter technique typically involves pouring a dose of liquid adrenaline into the subject's trachea. However, this method usually results in less active ingredient being ultimately delivered to the subject, as only a small proportion of the dose flows to the alveoli where it can be subsequently absorbed.

In addition, it is recommended that adrenaline be administered immediately in the event of cardiac arrest, and furthermore that adrenaline be administered until a normal rhythm is restored in accordance with the abovementioned practice guidelines. In this regard, any time spent finding an appropriate vein and waiting for the blood to circulate to the heart under the influence of saline, or waiting for a liquid dose to flow into the alveoli, perfuse into the blood stream and travel to the heart, can adversely impact a subject's expected outcome.

Other methods of adrenaline administration include intraosseous infusion, administration via a central line, and the like. However, such methods typically require advanced medical training and specialist apparatus.

It can also be desirable to administer adrenaline in other situations such as when a subject is experiencing anaphylaxis. Generally, it can be desirable to administer dry powder in other scenarios in which a subject is unresponsive, such as when in a diabetic coma, epileptic seizure, opioid overdose or the like. More generally, it can also be desirable to administer medicaments and vaccinations which are in the form of dry powder to responsive and conscious subjects, such as measles vaccine, Hepatitis B vaccine, insulin, antibiotics or the like.

US2013/0213397 describes a powdered medicament inhaler that may include a powder storage region, an inlet channel, a dispersion chamber, and an outlet channel. The geometry of the inhaler may be such that a flow profile is generated within the dispersion chamber that causes an actuator to oscillate, enabling the actuator when oscillating to deaggregate powdered medicament within the dispersion chamber to be aerosolized and entrained by the gas and delivered to a patient through the outlet channel.

US2008/0135047 describes methods and devices for assisting in the delivery of medicaments to the lungs of a patient are provided using a non-aerosol, inhalation device. In one embodiment, the methods and device utilize a positive pressure device that is effective to drive a medicament contained within a chamber in an inhalation device through an outlet and into a patient's lungs, either orally, through the patient's nasal passages, or through a tracheal tube in communication with the patient's lungs. In another embodiment, the present invention provides a connector for coupling an inhalation device to a tracheal tube to allow a medicament contained within a drug chamber in the inhalation device to be delivered to the patient's lungs via the tracheal tube.

US2011/0126830 describes a delivery device for delivering a metered amount of substance, the delivery device comprising: a mouthpiece through which a user in use exhales; an outlet through which substance is in use delivered; a housing fluidly connected to the mouthpiece and the outlet, such, that exhalation by the user through the mouthpiece creates an gas flow through the housing and from the outlet; and a substance-dispensing unit which is disposed within the housing and operative to dispense a metered amount of substance into an entraining gas flow as created through the housing.

US2010/0006095 describes apparatus and methods for delivering a powdered medicament for inhalation. The medicament is put in a receptacle on a vibration generator operated by fluid pressure, e.g. by means of an eccentric rotor. A flow of gas from a pressurized gas cylinder is passed into the receptacle, producing in concert with the vibration an aerosol which passes out of the receptacle and along a tube to be inhaled by the patient. Both the gas flow supply and vibration may be subject to the operation of a control unit, which may time the production of the aerosol according to a patient's breathing cycle, e.g. as part of a ventilator system.

US2011/0308516 provides a delivery device for a medicament comprising a housing, a receptacle holding a medicament in the form of a powder and a source of propellant, characterized in that the housing provides an inlet and an outlet for the receptacle wherein the inlet is in fluid communication with the source of propellant and is directed against the medicament and the outlet is spaced from the medicament to allow aerosolisation of the medicament; the device provides improved delivery efficiency, particularly a delivered fine particle fraction of greater than 20% by weight.

U.S. Pat. No. 6,003,512 describes an apparatus and method for aerosolizing and dispensing powders utilizing the forces of pressurizing and depressurizing gas loaded into powder agglomerates located in an enclosed powder chamber. Methods include administering peptides, genes, vitamins, and polymers into the peripheral lung. Also describes powder supply apparatus and method for single dose and repetitive applications.

WO2015/085362 describes an apparatus for use in administering a powdered medicament to a biological subject's airway, the apparatus including an inlet that in use is in fluid communication with a supply of positive pressure gas, an outlet that in use is in fluid communication with the subject's airway to deliver the positive pressure gas thereto and a medicament supply that provides a dose of powdered medicament so that the powdered medicament is entrained in a gas flow from the inlet to the outlet, thereby delivering the powdered medicament to the subject's airway.

U.S. Pat. No. 6,427,688 describes a dry powder inhaler having a dispersion chamber containing beads. A dose of powdered medicament is released into the chamber, or into an inlet tangentially joining into the chamber. As the patient inhales on a nosepiece or mouthpiece, gas moves circularly through the dispersion chamber to drive the beads. The beads roll, bounce, and collide repeatedly with the drug particles on the chamber surfaces or on the beads. The smaller active drug particles are separated from the larger carrier particles and from each other, and a powder aerosol is created and inhaled by the patient. The beads are preferably lightweight, so that they can be rapidly accelerated and moved, even with nominal inspiration. The flow resistance of the inhaler is also reduced via the beads, allowing greater gas flow and powder dispersion, without any increased effort by the patient.

SUMMARY OF THE PRESENT INVENTION

The present invention broadly provides a delivery device for administration of a particulate substance or composition to a biological subject. A method of delivering a dose of a particulate substance or composition to a biological subject using a delivery device is also broadly provided. The invention further broadly provides a container releasably storing, or suitable for releasably storing, a particulate substance or composition.

The particulate substance or composition as described herein may take any suitable form. The following aspects refer to a dry powder, which is preferred. It will be appreciated, however, that any suitable particulate medicament may be used.

In a first aspect, the present invention provides a delivery device for use in administering a dry powder to a biological subject's airway, the device comprising:
a) a housing having an inlet in fluid communication with an outlet for delivering a flow of gas to the subject's airway; and
b) one or more cantilever structures located within the housing, wherein vibration of the one or more cantilever structures facilitates entry of the dry powder into the flow of gas, such that the dry powder can be delivered by the flow of gas through the outlet to the subject's airway.

Preferably, the gas flow through the housing causes the one or more cantilever structures to vibrate. Preferably the gas flow causes the cantilever structure to undergo forced vibration.

Preferably, the one or more cantilever structures are reeds. In a particularly preferred embodiment, the device comprises a single said cantilever structure. In another embodiment, the device comprises two or more said cantilever structures.

Preferably, the vibration of the cantilever structure occurs with the gas flow over a range of gas flow rates. Preferably, the gas flow rates are commensurate with those provided by one or more expected sources of gas supply.

Preferably, the forced vibration, and subsequent resonance with gas pressure waves, generates a noise that provides audible feedback to a user.

In certain embodiments, the device comprises a container for storing a dose of dry powder. Preferably, the container is engaged or engageable with the housing so as to cover an opening in the housing located part way between the inlet and the outlet. Preferably, the container is configured to be at least partially rupturable or peelable to allow the dose of dry powder to be released into the housing via the opening.

In embodiments wherein the device comprises a container, suitably, release of the dose of the dry powder from the container results in at least a portion of the dry powder being in proximity to the one or more cantilever structures.

In certain embodiments, the one or more cantilever structures are capable of storing a dose of dry powder. Suitably, vibration of the cantilever structures releases at least a portion of the dry powder from the cantilever structure. Preferably, the one or more cantilever structures comprise one or more, preferably a plurality, of indentations for storing the dry powder.

In said embodiments, suitably, the device further comprises a removable restraint for constraining or preventing vibration of the cantilever structure prior to use.

Preferably, the dry powder is deagglomerated within the housing by the vibration of the cantilever structure, prior to delivery to the subject's airway.

Preferably, the housing further comprises a deagglomerating surface, wherein the one or more cantilever structures vibrate against, or in close proximity to, the deagglomerating surface. Suitably, vibration of the cantilever structure in close proximity to the deagglomerating surface forces the dry powder between the cantilever structure and the deagglomerating surface, thereby at least partially deagglomerating the dry powder.

In embodiments, the housing of the delivery device comprises a filter in the form of one or more openings, for allowing particles of the dry powder of a maximum size to pass through the filter.

Typically, the opening(s) of the filter are defined by at least one of:
a) a single slot;
b) a plurality of slots;
c) a plurality of holes; and,
d) a mesh.

In embodiments, the filter of the device is, or is of, the deagglomerating surface of the device.

In embodiments, the housing further comprises an eddy generating structure. Suitably, the eddy generating structure is disposed downstream of the deagglomerating surface and/or filter. Preferably, eddies generated by the eddy generating promote deagglomeration of the entrained dry powder. Preferably the eddies are high energy eddies. Preferably, the eddies promote deagglomeration by fluid turbulence.

In embodiments, the eddy generating structure comprises an array of spaced apart and/or parallel fixed members, preferably forming a staggered arrangement. Preferably, the fixed members are elongate members.

In embodiments, the fixed members that form the eddy generating structure are disposed beneath the deagglomerating surface and/or filter, preferably in abutment therewith.

In embodiments, one or more of the fixed members of the eddy generating structure are aligned with respective slots in the deagglomerating surface and/or filter.

Preferably, the fixed members extend the length of the deagglomerating surface and/or filter.

Preferably, the fixed members are arranged so as to promote vortex shedding.

In embodiments, the device comprises at least one of:
a) a one-way valve;
b) an exhalation valve; and,
c) an adaptor that provides a mechanism to attach a valve, for preventing reverse flow of the gas through the inlet.

In embodiments, the device comprises at least one inlet adapter for coupling the device to a further component, preferably wherein said further component is at least one of:
a) a Bag-Valve-Mask (BVM);
b) a resuscitation bag;
c) a ventilator;
d) an oxygen pump;
e) a compressed gas supply;
f) an automatic resuscitator;
g) a manual resuscitator; and,
h) a reservoir outlet piece.

In embodiments, the device comprises at least one outlet adapter for coupling the apparatus to a further component, preferably wherein said further component is at least one of:
a) a mask;
b) a tracheal tube, such as an endotracheal tube;
c) a supraglottic airway or the like, such as laryngeal airway.

In embodiments, at least one of the inlet adaptor and the outlet adaptor comprises a universal adaptor.

Preferably, the dry powder is or comprises at least one of:
a) adrenaline;
b) glucose;
c) glucagon;
d) benzodiazepine;
e) phenytoin;
f) salbutamol;
g) insulin;
h) naloxone; and,
i) flumazenil.

Preferably, the device is for the treatment of at least one of:
a) cardiac failure;
b) hypoglycaemia;
c) anaphylaxis;
d) epilepsy;
e) chronic obstructive pulmonary disorder;
f) asthma;
g) bronchitis;
h) drug overdose; and,
i) diabetes induced coma.

Preferably, the gas is supplied in accordance with artificial respiration of the subject.

Preferably, a supply of positive pressure gas is received through the inlet and delivered to the subject's airway, via the outlet.

In embodiments, the supply of positive pressure gas is provided by any one of:
a) a bag-valve-mask (BVM);
b) a resuscitation bag;
c) an exhalation valve;
d) a ventilator;
e) an oxygen pump;
f) a compressed gas supply;
g) an automatic resuscitator;
h) a manual resuscitator; and,
i) an operator exhaling in fluid communication with at least one of the inlet, a reservoir outlet piece, and a mask.

In preferred embodiments, the gas flow delivers dry powder into the subject's lungs without requiring the subject to inhale.

In embodiments, a supply of negative pressure gas is provided by subject inhalation.

In a second aspect the present invention provides a method of delivering a dose of dry powder to a biological subject using a delivery device, the delivery device comprising a housing having an inlet in fluid communication with an outlet and one or more cantilever structures located within the housing, the method including the steps of:
 a) generating a flow of gas between the inlet and outlet;
 b) vibrating the one or more cantilever structures to facilitate entry of the dry powder into the flow of gas; and
 c) delivering dry powder entrained in the gas flow to the subject's airway.

Suitably, according to the method of this aspect, the step of generating the flow of gas between the inlet and the outlet facilitates vibration of the one or more cantilever structures.

In an embodiment of the method of this aspect, the dry powder is contained within a container of the device engaged with the housing so as to cover an opening in the housing located part way between the inlet and the outlet, and the method includes the step of at least partially rupturing the container to allow the dose of dry powder to be released into the housing via the opening, whereby at least a portion of the dry powder engages with the one or more cantilever structures.

In said embodiment, the method may include the steps of: pausing the gas flow after the subject has completed an exhalation and before causing the container to be ruptured; and resuming the gas flow after the container has been ruptured so as to entrain the dry powder in the gas flow.

In an embodiment of the method of this aspect, the one or more cantilever structures stores the dose of dry powder, and vibration of the cantilever structures releases at least a portion of the dry powder to facilitate entry of at least a portion of the dry powder into the flow of gas.

In said embodiment, the method of this aspect may include the step of removing a restraint for constraining or preventing vibration of the cantilever structure, prior to step (a) and/or step (b).

Preferably, delivering the dry powder into the subject's lungs does not require the subject to inhale.

Preferably, the gas flow is delivered in an amount corresponding to an artificial breath.

In an embodiment, the dry powder is delivered into the subject's lungs by way of inhalation.

In a third aspect, the invention provides a container releasably storing, or suitable for releasably storing, a particulate substance or composition, the container comprising a shell sealed by a seal in which the particulate substance or composition is or can be releasably stored, wherein a puncturing device for rupturing the seal to release the particulate composition is housed within the shell.

Preferably, the particulate substance or composition is a dry powder.

Preferably, the shell is a blister shell.

Preferably, the puncturing device is a ring or cup structure that fits within the shell.

Preferably, the puncturing device is attached to the shell to prevent or constrain the puncturing device from separating from the shell upon depression.

Suitably, in use, the shell is depressed by a user whereby the puncturing device pierces the seal, thereby releasing the particulate composition from the container.

Suitably, the container protects the dry powder from one or more of moisture, oxidation, and photo-degradation.

Preferably, the container is configured to be a single-use container.

Preferably, the container is for use with the delivery device of the first aspect.

It will be appreciated that the above aspects of the invention and their respective features can be used in conjunction, interchangeably and/or independently, and reference to separate aspects in not intended to be limiting.

It will be appreciated that the indefinite articles "a" and "an" are not to be read as singular indefinite articles or as otherwise excluding more than one or more than a single subject to which the indefinite article refers.

Throughout this specification and claims which follow, unless the context requires otherwise, the word "comprise", and variations such as "comprises" or "comprising", will be understood to imply the inclusion of a stated integer or group of integers or steps but not the exclusion of any other integer or group of integers.

BRIEF DESCRIPTION OF THE DRAWINGS

Examples of the present invention will now be described with reference to the accompanying drawings, in which:

FIG. 15 is a flow chart of an example of a method of delivering a dose of dry powder to a biological subject using a delivery device as described herein;

FIG. 25 sets forth comparative data on Inspiratory Flow Rate and Intrinsic Resistance for a range of delivery devices;

DETAILED DESCRIPTION OF THE PREFERRED EMBODIMENTS

Figure 1A:
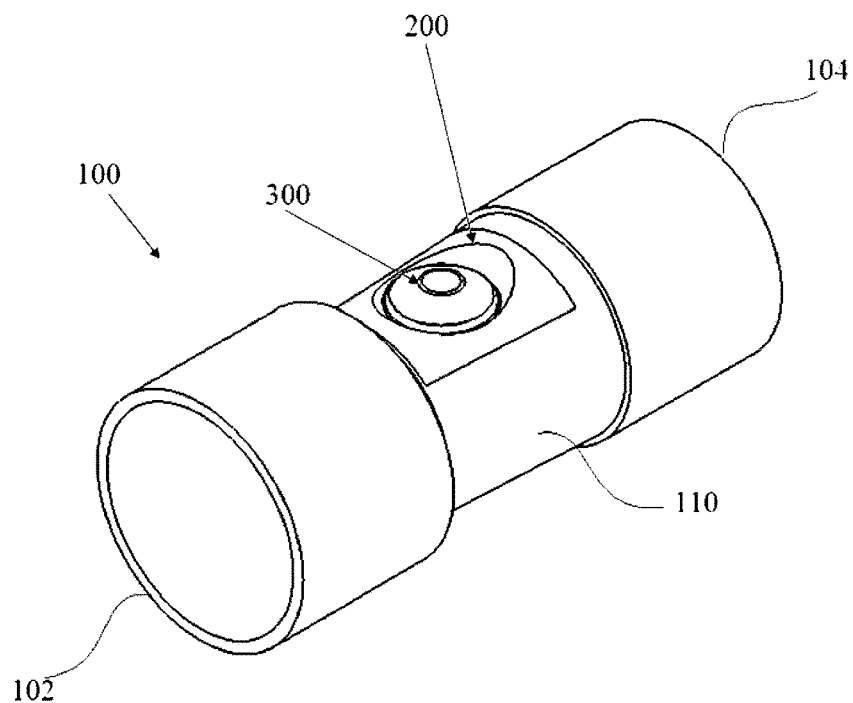
FIG. 1A is a perspective view of an example of a delivery device comprising a container, for use in administering a dry powder to a biological subject's airway.

Exemplary embodiments of a delivery device 100 for use in administering a particulate medicament, such as a dry powder, to a biological subject's airway will now be described, with reference to the figures and examples. As used herein, and as will be understood by the skilled person, "dry powder" refers generally to a form of particulate medication for respiratory delivery, that is typically delivered in the absence of propellant.

The dry power or particulate medicament will suitably comprise at least one "active ingredient", i.e. a component with biological activity. The dry powder or particulate medicament may be in the form of one or more pure, or substantially pure, active ingredients. Alternatively, the dry powder or particulate medicament may include one or more pharmaceutically acceptable components in addition to one or more active ingredients, e.g. fillers, excipients, or diluents, as are well known in the art. For a non-limiting overview of dry powder formulations, the skilled person is directed to Telko and Hickey (2005) 'Dry Powder Inhaler Formulation' *Respiratory Care,* 50(9), 1209-1227, incorporated herein by reference.

As seen in FIGS. 1-12, the delivery device 100 comprises a housing 110 having an inlet 102 in fluid communication with an outlet 104 for delivering a flow of gas to the subject's airway. The delivery device 100 further comprises a cantilever structure 140 located within the housing, as most clearly seen in FIG. 6.

With reference to FIGS. 6-10, the cantilever structure 140 is in the form of one or more flexible members, e.g. reeds, comprising a free end, and capable of vibrating. Vibration of the cantilever structure facilitates entry of the dry powder into the flow of gas, whereby the dry powder is delivered entrained in the flow of gas to the subject's airway.

As herein described, with reference to the figures and examples, the cantilever structure 140 offers significant advantages in the context of delivery device 100. However, although not preferred, it will be appreciated that in alternative embodiments, a different arrangement of flexible member(s) capable of vibrating can be used.

Typically, the gas flow through the housing 110 causes the cantilever structure 140 to undergo forced vibration. When undergoing forced vibration, the cantilever structure 140 (e.g. in the form of one or more reeds) moves rapidly between deflected positions, as shown in FIG. 6, in resonance with gas pressure waves.

Typically, prior to delivery to the subject's airway using delivery device 100, the dose of dry powder is deagglomerated within the housing 110. As used herein "deagglomerate", "deagglomeration", "deagglomerated", and the like, will be understood to refer to a process of separating or dispersing multiple particles that are aggregated or clustered together. With reference to the examples, deagglomeration of particles prior to delivery may maximise efficacy of the delivery of dry powder using the delivery device. It will be appreciated that the dry powder may, but need not necessarily, be at least partially crushed prior to delivery. As used herein, "crush", "crushing", "crushed" and the like will be understood to refer to reducing an individual particle in size, typically by breaking the particle into individual smaller particles.

Forced vibration of the cantilever structure 140 as described above will suitably facilitate at least partial deagglomeration and/or crushing of the dry powder prior to delivery. To assist with deagglomeration of the dry powder by vibration of the cantilever structure 140, the housing 110 of the delivery device 100 will typically further comprise a deagglomerating surface 150, as seen most clearly in FIG. 6. The deagglomerating surface 150 will be configured such that suitable vibration of the cantilever structure 140 brings said structure into close proximity to the deagglomerating surface 150, wherein dry powder located between the cantilever structure 140 and the deagglomerating surface 150 is at least partially deagglomerated and/or crushed by the motion of the cantilever structure 140.

Typically, the deagglomerating surface 150 will be or comprise a filter having or in the form of a single or plurality of openings 152, as seen for example in FIGS. 7-10. The openings 152 will suitably allow the dry powder to pass into the gas flow after aggregates of dry powder have been deagglomerated and/or crushed to a size allowed by the filter. The plurality of openings 152 may take any suitable form including for instance as one or more, or a plurality, of slots (as shown), one or more, or a plurality, of holes, or a wire mesh. The presence of a filter prevents or constrains larger aggregates from proceeding through the delivery device 100 to be delivered to a subject, without first being deagglomerated and/or crushed.

In typical embodiments wherein the gas flow through the housing 110 causes the cantilever structure 140 to undergo forced vibration as hereinabove described, a system of resonance results which repeatedly transfers energy between the gas and the cantilever structure 140, with excess energy used to deagglomerate the powder. It will be understood that, during this process, the cantilever structure 140 typically adopts a mode of vibration within the device. Any suitable mode of vibration of the cantilever structure may be induced (e.g. first, second, third, or others) in accordance with the selection of relevant design parameters.

Typically, a substantial portion of the dry powder delivered by the delivery device 100 is deagglomerated to a suitable size. Typically, said suitable size will be from about 1 μm to about 100 μm. In some embodiments, said suitable size may less than about: 90, 80, 70, 60, 50, 40, 30, 20, 10, 9, 8, 7, 6, 5, 4, 3, 2, or 1 μm.

In some preferred embodiments, said suitable size may be an original particle size. As used herein, an "original particle size" will be understood to refer to the particle size of a dry powder as originally produced, e.g. before storage. It will be appreciated that storage of a dry powder, either prior or after placement of the dry powder within the delivery device 100 (as described in more detail below) can result in substantial collection, clustering or agglomeration of the dry powder, such that many or all of the particle may be larger than the original particle size.

Preferably, at least 20% of the dry powder delivered by the delivery device is deagglomerated to an original particle size or otherwise suitable particle size. In embodiments, at least: 30, 40, 50, 60, 70, 80, or 90%, or even greater, of the dry powder delivered by the delivery device is deagglomerated to an original or otherwise suitable particle size.

The cantilever structure 140 will have an "operating range", referring to the range of gas flow rates within which the cantilever structure 140, e.g. reed, effectively resonates or vibrates. Preferably, the operating range includes up to about 120 L/min, or even greater such as up to about: 130, 140 or 150 L/min. In some preferred embodiments the operating range includes about 70 L/min or less, such as about: 60, 50, 40, 30, or 20 L/min. In some preferred embodiments, the operating range includes about 20 L/min or less, such as about: 15, 10, or 5 L/min. In an embodiment, the operating range is or includes about 50 L/min to about 120 L/min. In an embodiment, the operating range is or includes about 70 L/min to about 120 L/min. In one preferred embodiment, the operating range is or includes about 20 L/min to about 120 L/min. In one preferred embodiment, the operating range is or includes about 10 L/min to about 140 L/min.

The resonance pattern and/or operating range of the cantilever structure 140 will typically be dependent on a number of parameters, including shape, tip clearance, length, thickness, width, stiffness, and/or symmetry of the cantilever structure 140; the ratio of the area of the cantilever structure 140 to the area of the deagglomerating surface 150 and/or opening 152; the shape and/or volume of the housing 110; and/or material properties, particularly of the cantilever structure 140.

Figure 5A:
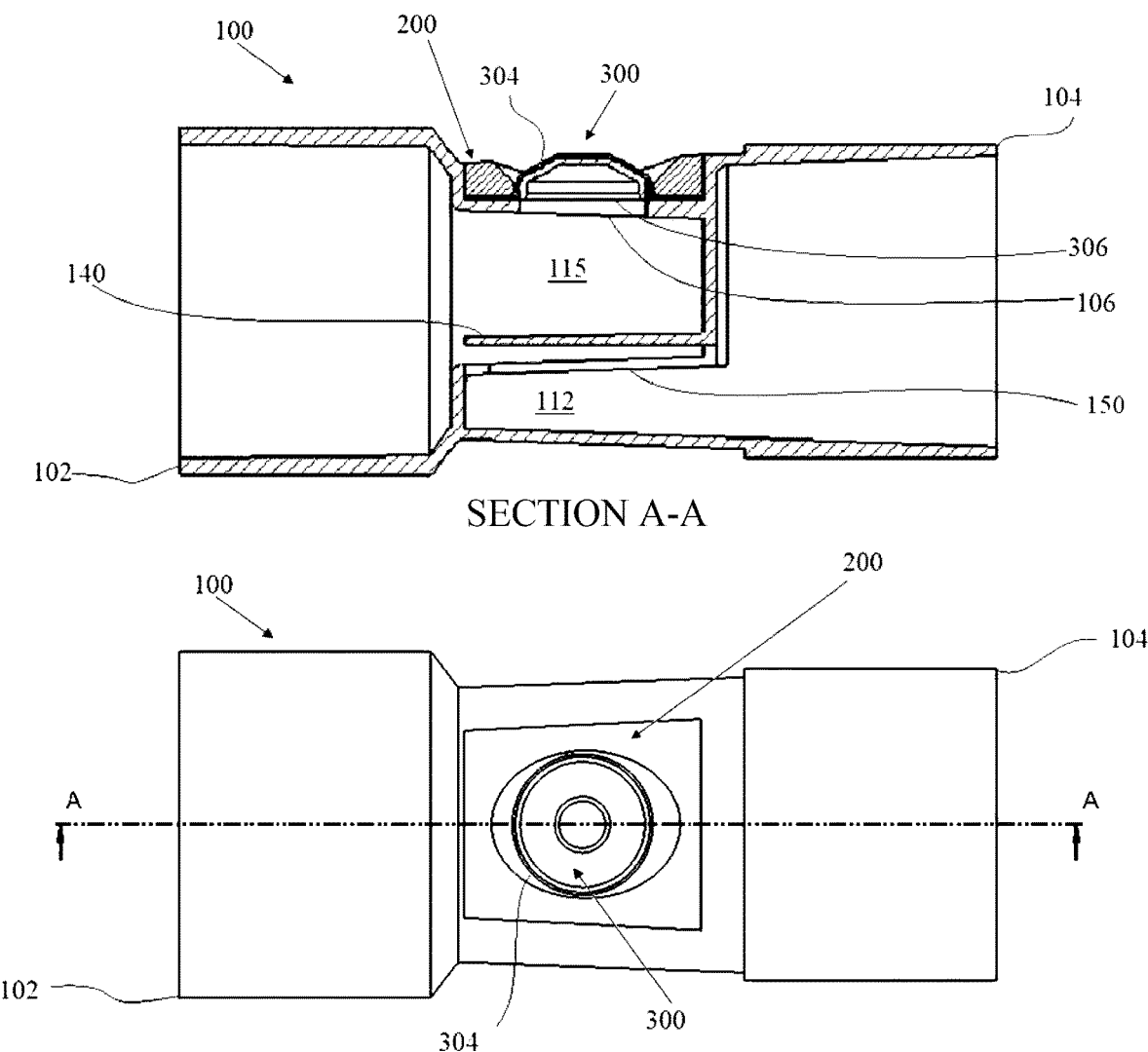
FIG. 5A shows respective cross sectional side view and top view of an example of a delivery device without an eddy generator structure.
Figure 5B:
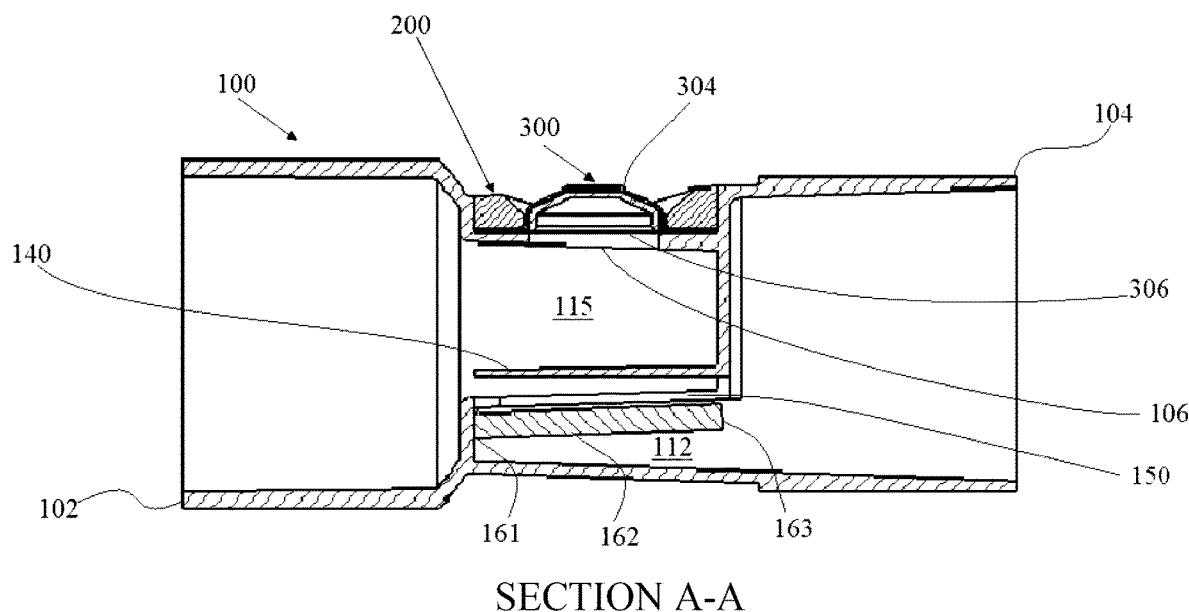
FIG. 5B shows respective cross sectional side view and top view of an example of a delivery device with an eddy generator structure.
Figure 5B:
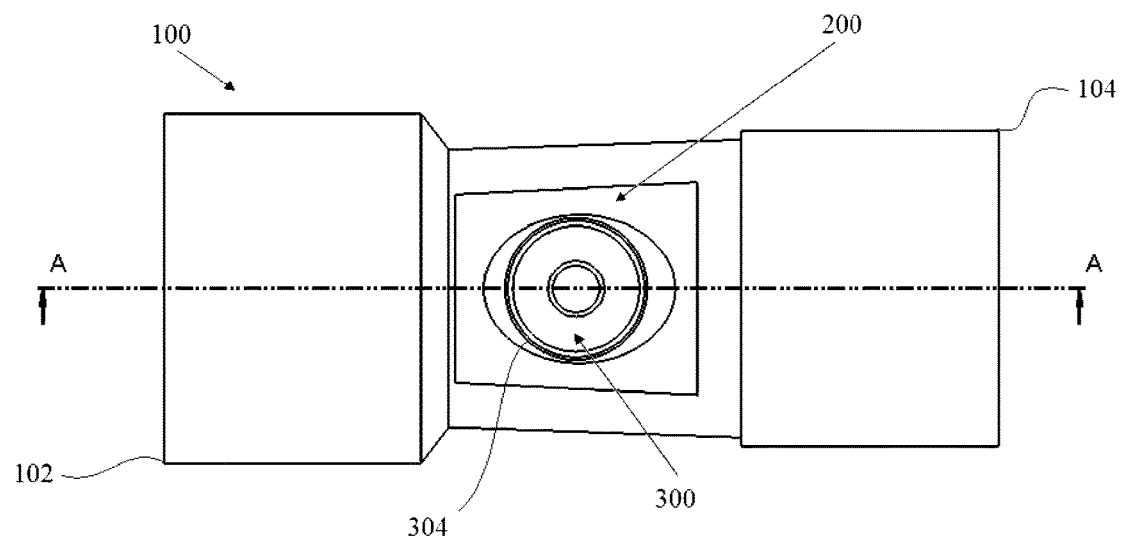

Typically, the orientation of free end 144 of the cantilever structure 140 toward oncoming air from the inlet 102, as seen for example in FIG. 5, is particularly advantageous for achieving desired resonance and/or operating range of the cantilever structure 140. This arrangement of the cantilever structure 140 is considered to be effective for producing an unstable condition that encourages start-up vibrations and resonance, and adoption of a desired standing wave pattern of resonance.

Figure 19:
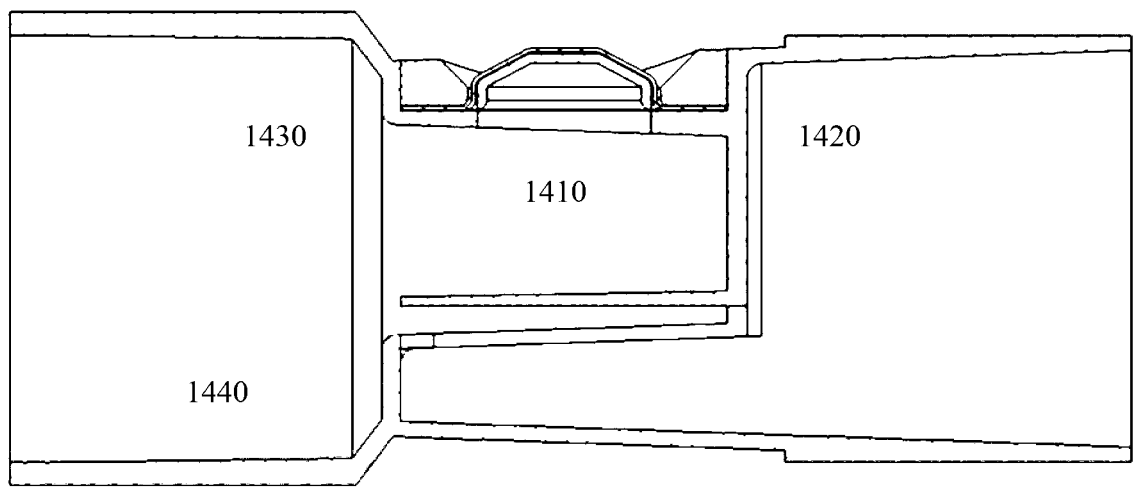
FIG. 19 sets forth parameters of a cantilever structure arrangement according to an exemplary embodiment of the delivery device.
Figure 19:
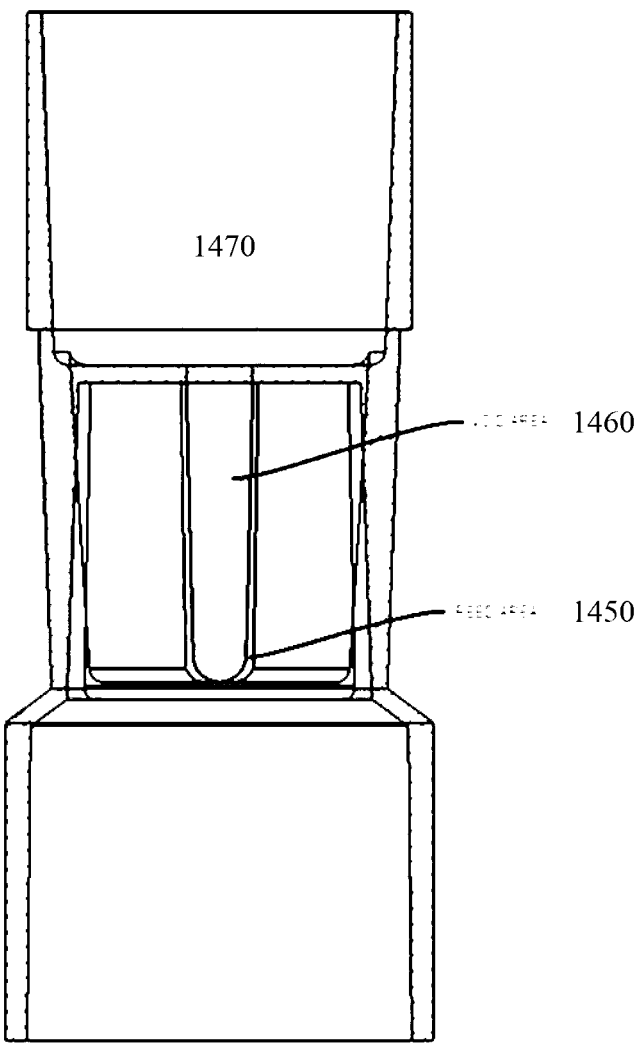
Figure 20:
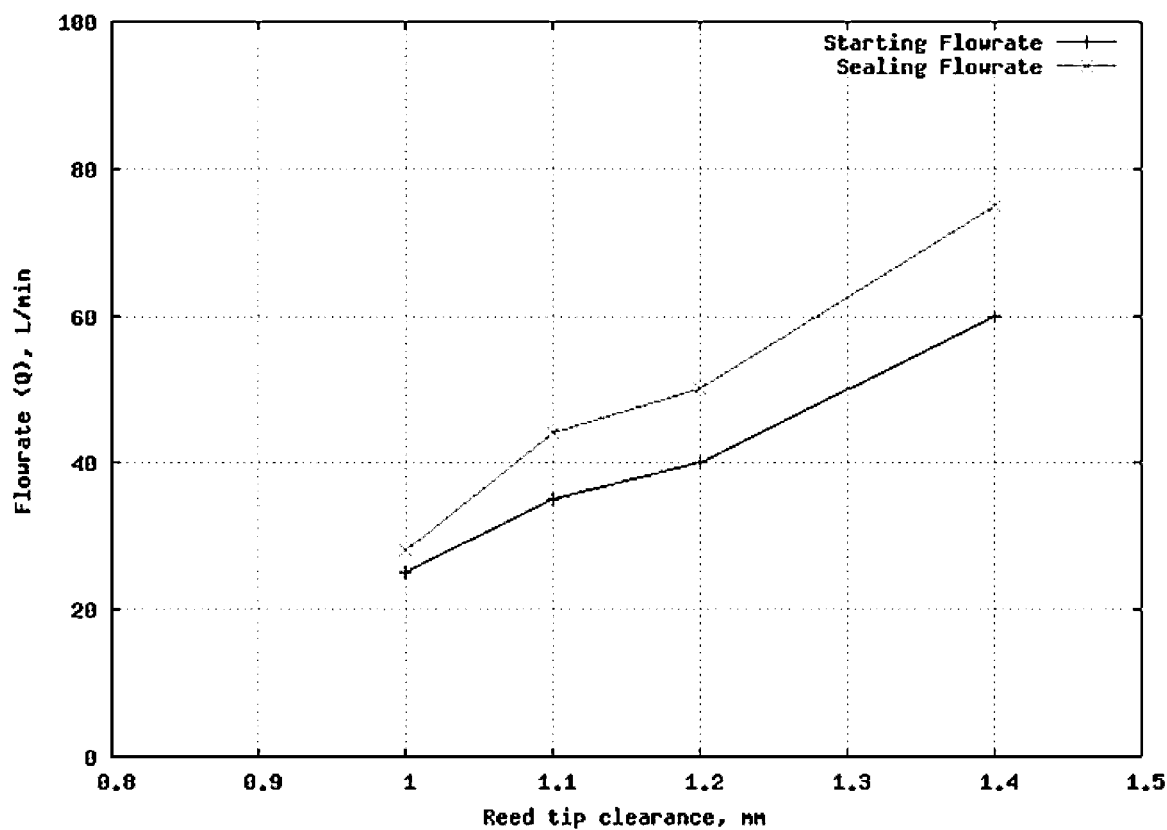
FIG. 20 sets forth data on the effect of cantilever tip clearance on starting flow rate.
Figure 21:
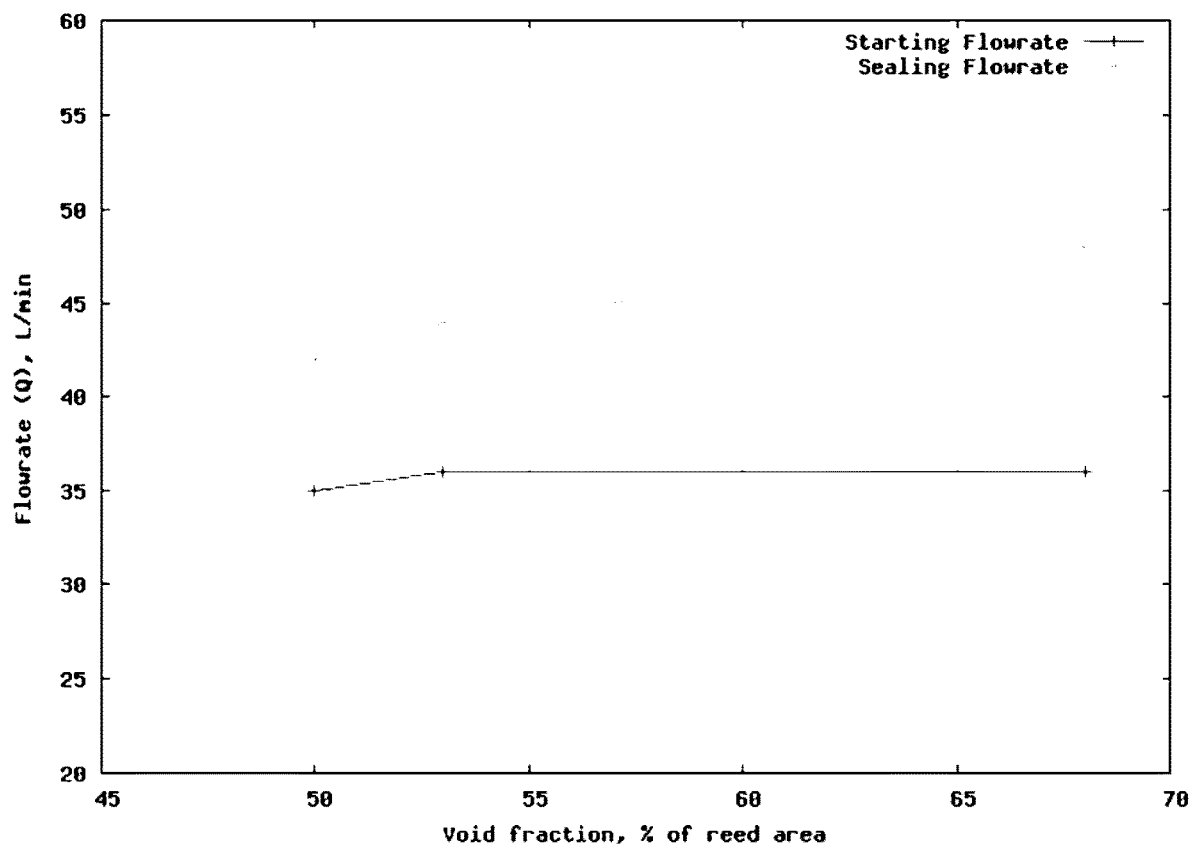
FIG. 21 sets forth data on the effect of the ratio of void area to reed area on starting flow rate.
Figure 22:
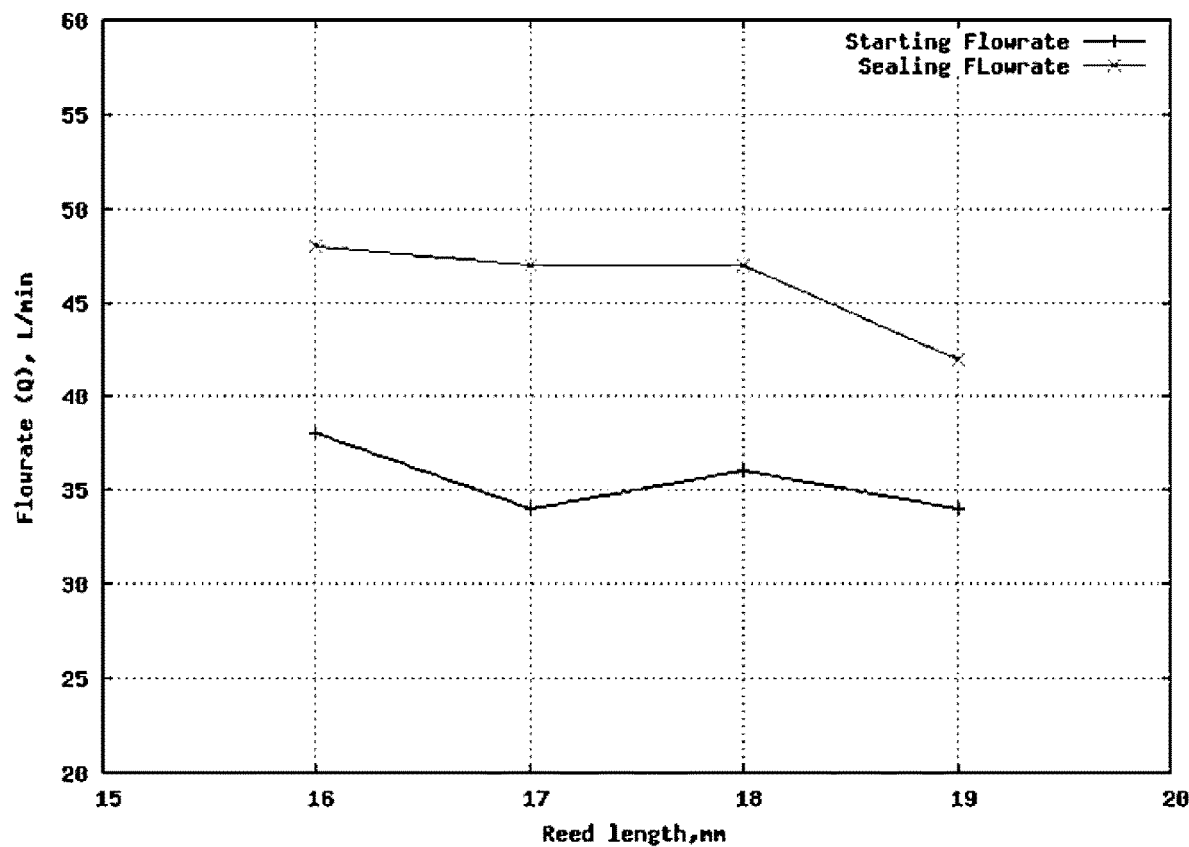
FIG. 22 sets forth data on the effect of cantilever structure length on starting flow rate.
Figure 23:
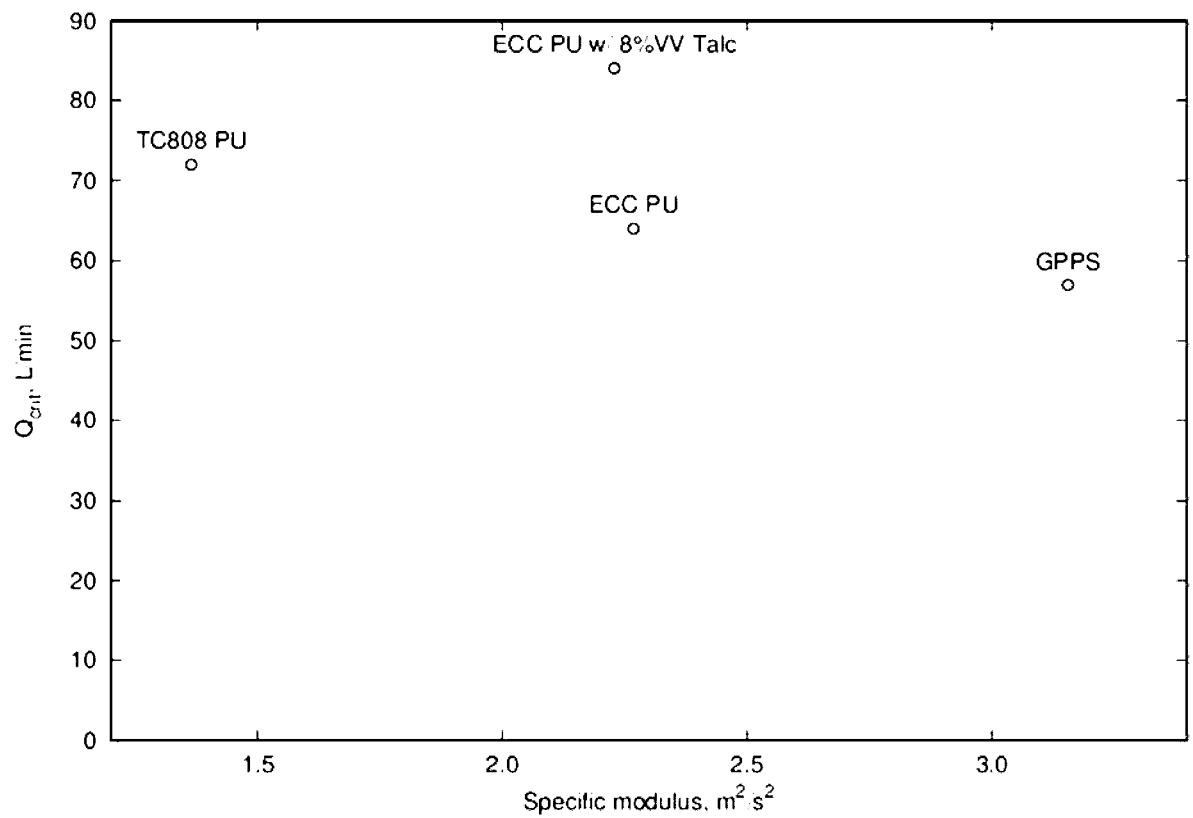
FIG. 23 sets forth data on the effect of specific modulus on starting flow rate.
Figure 24:
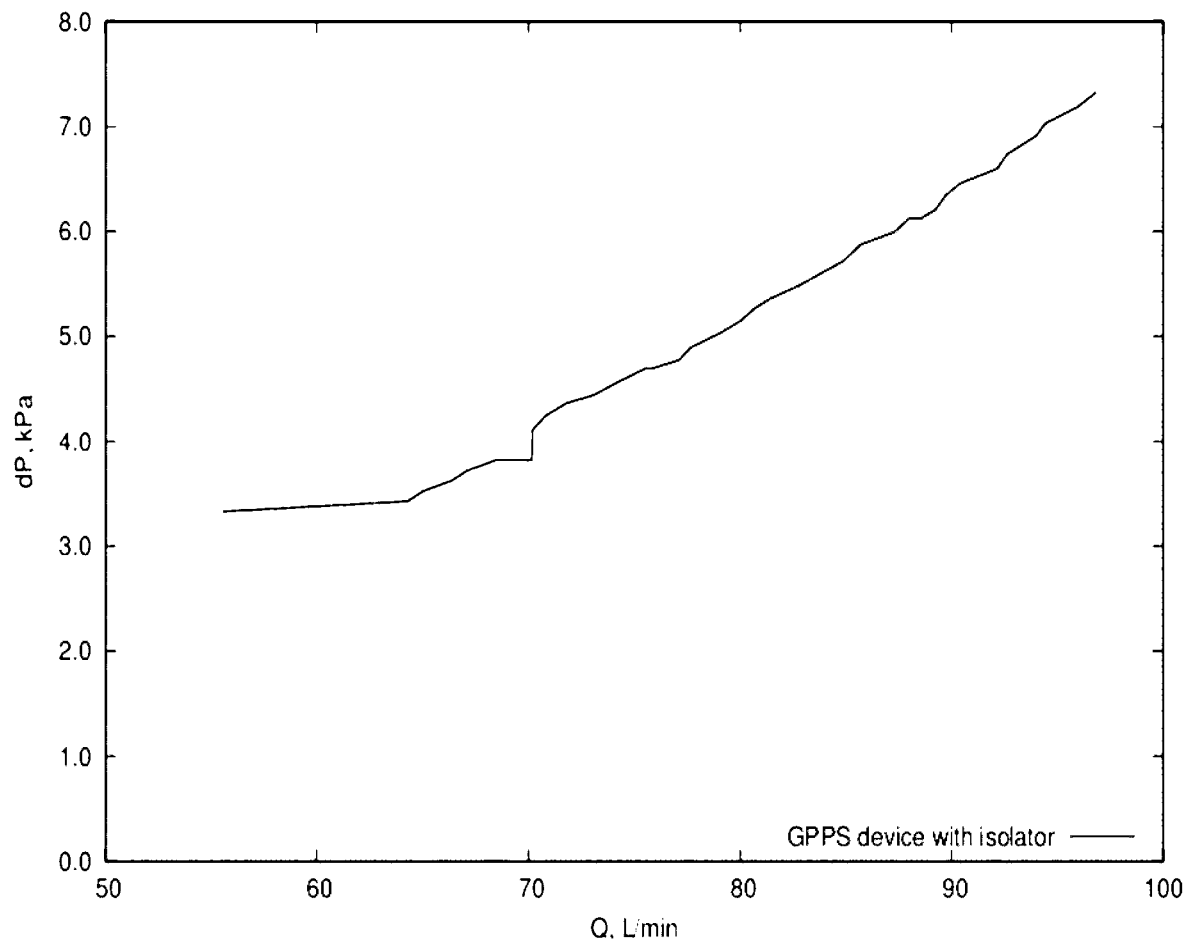
FIG. 24 sets forth data on pressure drop in an embodiment of the delivery device for a range of flow rates.

As set out in the examples and with reference to FIG. 19, embodiments of the delivery device will have parameters in regard to cantilever structure (or reed) length 1410; root thickness 1420 and tip thickness 1430; tip clearance 1440; reed area 1450; void area 1460; and width 1470.

Preferably, the cantilever structure tip clearance 1440 is between about 0.1 mm to about 5 mm, including about: 0.2, 0.4, 0.6, 0.8, 1, 1.2, 1.4, 1.6, 1.8, 2, 2.2, 2.4, 2.6, 2.8, 3, 3.2, 3.4, 3.6, 3.8, 4, 4.2, 4.4, 4.6, and 4.8 mm. More preferably, said tip clearance is between about 0.25 mm to about 4.5 mm. Even more preferably, said tip clearance is between about 0.5 mm and about 4 mm.

Preferably, the cantilever structure length 1410 is between about 1 mm and about 100 mm, including about 5, 10, 15, 20, 25, 30, 35, 40, 45, 50, 55, 60, 65, 70, 75, 80, 85, 90 and 95 mm. More preferably, said length is between about 5 mm and about 40 mm. Even more preferably, said length is between about 10 mm and about 30 mm.

Preferably, the void area 146 to cantilever structure area 145 ratio is between about 0.01 to about 1.75, including about: 0.05, 0.1, 0.15, 0.2, 0.25, 0.5, 0.75, 1, 1.25, and 1.5. More preferably, said ratio is between about 0.25 to about 1.25. Even more preferably, said ratio is between about 0.4 to about 1.1.

Preferably, the root thickness 1420 is between about 0.05 mm and about 10 mm, including about 0.1, 0.2, 0.3, 0.4, 0,5, 0.6, 0.7, 0.8, 0.9, 1, 1.5, 2, 2.5, 3, 3.5, 4, 4.5, 5, 5.5, 6, 6.5, 7, 7.5, 8, 8.5, 9, and 9.5 mm.

Preferably, the tip thickness 1430 is between about 0.05 mm and about 5 mm, including about 0.1, 0.2, 0.3, 0.4, 0,5, 0.6, 0.7, 0.8, 0.9, 1, 1.5, 2, 2.5, 3, 3.5, 4, 4.5, and 5 mm.

Typically, as seen in FIGS. 7-10, the cantilever structure 140 becomes thinner towards the free end 144. This can assist with achieving initial vibration.

The cantilever structure 140 may comprise an asymmetry, such as uneven side lengths. This can increase the likelihood of a torsional mode of vibration, which may assist with achieving initial vibration.

The material used to form the cantilever structure 140 will preferably have elastic modulus; density; and/or specific modulus within particular respective ranges. Preferably, the elastic modulus is between about 0.5 to about 250 GPa, including about: 1, 2, 3, 4, 5, 6, 7, 8, 9, 10, 20, 30, 40, 50, 60, 70 80, 90, 100, 110, 120, 130, 140, 150, 160, 170, 180, 190, 200, 210, 220, 230, and 240 GPa. In some embodiments, the elastic modulus is between about 1 to about 5 GPa. In some preferred embodiments, the elastic modulus is about 4 GPa.

Preferably, the density is between about 0.1 and about 3 $g/cm^3$, including about: 0.5, 1, 1.5, 2, and 2.5 $g/cm^3$. In some embodiments, the density is between 0.5 and 1.2 $g/cm^3$. Preferably the specific modulus is between about 0.5 and about 100, including about: 1, 1.5, 2, 2.5, 3, 3.5, 4, and 4.5, 5, 5.5, 6, 6.5, 7, 7.5, 8, 8.5, 9, 9.5, 10, 15, 20, 25, 30, 35, 40, 45, 50, 5, 60, 65, 70, 75, 80, 85, 90, and 95. In some embodiments, the specific modulus is between about 1 and about 4.

Preferably, the cantilever structure has a damping ratio of less than about 0.5, including less than about: 0.45, 0.4, 0.35, 0.3, 0.25, 0.2, 0.15, 0.1, and 0.05.

Without limitation, suitable material to achieve the above parameters can include polymers and metals, or composites thereof. Suitable polymers include thermoplastics, such as polycarbonate, polypropylene, acrylic, and polystyrene, as set forth in the examples.

In preferred embodiments of delivery device 100 and cantilever structure 140 thereof as described herein, the operating range is designed to be optimal for both patient dosage and resuscitation. It will be understood that the flow of gas (typically air) may be supplied to the delivery device 100 by any suitable mechanism, for example, a Bag-Valve-Mask (BVM) (e.g. Ambu-bag), a resuscitation bag, a manual resuscitator, an automatic resuscitator, an operator exhaling in fluid communication with the inlet and/or a mouthpiece or mask in communication with the inlet, a ventilator, an oxygen pump, a compressed gas supply, or the like. The gas or air may be supplied by a positive pressure source as described above that is connected to the inlet 102, or a negative pressure source such as when a subject is able to inhale themselves via the outlet 104.

Preferably, suitable forced vibration of cantilever structure 140 for effective delivery of dry powder using delivery device 100 occurs over a range of gas flow rates commensurate with those typical of an artificial breath.

In the embodiment of delivery device 100 shown in FIG. 1, the housing 110 further comprises an opening 106 part way between the inlet 102 and outlet 104, and a container or store 300, best seen in FIG. 4 and described in further detail below, placed covering the opening 106. In this embodiment, the container 300 stores the dose of dry powder. The container 300 engages with the housing 110 so as to cover the opening 106 and is configured to be at least partially rupturable in use to allow the dose of dry powder to be released into the housing 110 via the opening 106, whereby it is entrained in the gas flow for delivery to the subject's airway.

In said embodiment, the container 300 is typically positioned over the opening 106 of the housing 110 so that a blister skirt 302 is in abutment with a blister seat 108 formed in a recessed portion of the housing 110. The store may be fixed thereto in any suitable manner such as through mechanical fastening, glue and the like. The container 300 is typically located and/or further secured in place by a collar 200.

Figure 14:
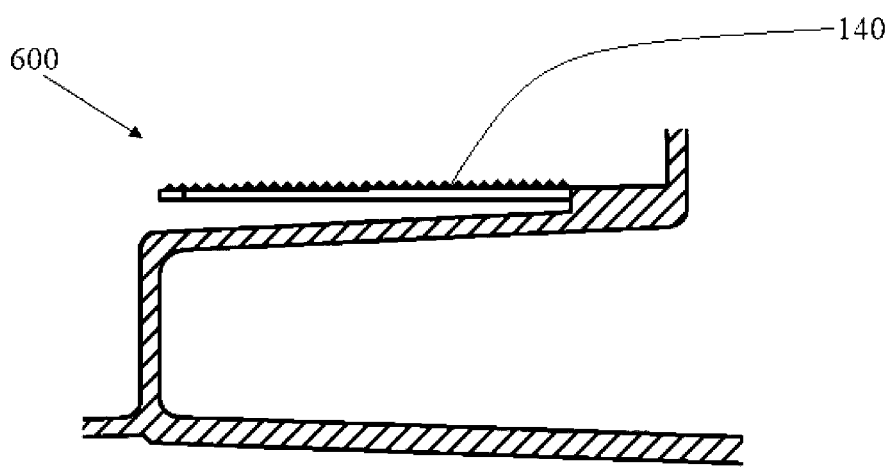
FIG. 14 is a cross sectional view of a delivery device with the medicament contained within indentations on the surface of a reed, and with a removable restraint fitted to the reed.

In alternative embodiments of delivery device 100, the dose of dry powder may be stored or otherwise located in or on one or more depressions or indentations of the cantilever structure 140. For example as depicted in FIG. 14, the cantilever structure 140 comprises a plurality of indentations wherein the dose of dry powder is located. Suitably, in these embodiments, the adhesion force between the cantilever structure 140 and the particles will be such that the medicament will only be released, or only released in substantial amount or quantity, when the cantilever structure 140 vibrates and/or impacts the deagglomerating surface 150. In these embodiments the device will typically not include the blister 300 or collar 200 shown in FIG. 14.

In said embodiments wherein the dose of dry powder is located in, on, or proximate to, the cantilever structure 140, preferably the cantilever structure 140 is supported by a removable restraint or insert 600 (as seen in FIG. 14), that is to be removed prior to use. The removable restraint 600 is adapted to prevent or constrain movement of cantilever structure 140.

Embodiments of delivery device 100 wherein the dose of dry powder is located in or on the cantilever structure 140 will preferably be sealed prior to use. For example, suitable removable seals (e.g. foil or plastic seals; not shown) may be placed over the cantilever structure 140, the inlet 102 and/or the outlet 104. This sealed arrangement can protect the dry powder from moisture, oxidation and/or photo- or chemical degradation prior to use.

In alternative embodiments of delivery device 100, the dose of dry powder may be stored in a capsule that is located within the device housing 110.

In alternative embodiments of delivery device 100, the dose of dry powder may be stored in a reservoir that is located within the device housing 110.

It will be appreciated that each of the preceding exemplary embodiments of storage of dry powder of the delivery device 100 may have particular advantages.

In each of these embodiments, a suitable or desired dosage of dry powder can be pre-loaded into delivery device 100. Pre-loading the medicament into the device can be particularly beneficial as it reduces the steps required by a user to deliver the drug to the subject. Pre-loading can also help ensure that the correct amount of dry powder is administered, which can minimise the risk of overdose.

In embodiments wherein the dry powder is stored in the container 300, the delivery device including the container 300 may be designed to be single-use. However, advantageously, it is also possible to replace container 300 after release of the dry powder. This can facilitate administration of multiple doses of dry powder, and/or re-use of the delivery device 100. It will be further appreciated that the ease of administration and/or the control thereof of the dose of dry powder using container 300 can be advantageous. In this regard, typically a user only needs to actuate the device with their thumb, for example by depressing the blister which causes a seal to be ruptured thereby releasing the stored dose of dry powder into the device housing.

In embodiments wherein the dry powder is located on or in the cantilever structure, the first use of the delivery device can produce a medicated breath. It will be appreciated that, in these embodiments, powder will suitably be held in or on the cantilever structure by adhesive forces between the powder and the reed, and by cohesive forces between the particles, but released when the cantilever structure vibrates and/or strikes the deagglomerating surface.

Advantageously, in embodiments wherein the dry powder is located in or on the cantilever structure, the amount of the emitted dose may be particularly reliable. By comparison, in embodiments wherein the delivery device includes the container 300, the emitted dose may be reduced, for example, if the device is tipped upside-down after the powder is released from the store. A further potential advantage of embodiments wherein the dry powder is located in or on the cantilever structure is that the dry powder particles can be stored with greater physical separation. This may reduce agglomeration of the powder due to adhesive forces, and potentially improve the Fine Particle Fraction of the emitted dose.

Another potential advantage of embodiments wherein the dry powder is located in or on the cantilever structure is that the device can be adapted such that dry powder will only be substantially released from the cantilever structure upon sufficient airflow for effective treatment of a subject. A further potential advantage of said embodiment is that the device can be adapted such that dry powder will only be substantially released from the cantilever structure when said structure is operating as intended.

The dry powder according to the present invention may include any suitable medicament for administering to the subject's airway, in accordance with the subject's condition and medical requirements. As hereinabove described, the dry powder may be in the form of one or more pure, or substantially pure, active ingredients. The dry powder may alternatively include one or more pharmaceutically acceptable components in addition to one or more active ingredients, e.g. fillers, excipients, or diluents, as are well known in the art.

Examples of active agents which may be delivered according to the present invention include beta-2-agonists, steroids such as glucocorticosteroids (preferably anti-inflammatories), anti-cholinergics, leukotriene antagonists, leukotriene synthesis inhibitors, pain relief drugs generally such as analgesics and anti-inflammatories (including both steroidal and non-steroidal anti-inflammatories), cardiovascular agents such as cardiac glycosides, respiratory drugs, anti-asthma agents, bronchodilators, anti-cancer agents, alkaloids (e.g. ergot alkaloids) or triptans such as can be used in the treatment of migraine, drugs (for instance sulphonyl ureas) useful in the treatment of diabetes type I and II and related disorders, sleep inducing drugs including sedatives and hypnotics, psychic energizers, appetite suppressants, anti-arthritics, anti-malarials, anti-epileptics, anti-thrombotics, anti-hypertensives, anti-arrhythmics, anti-oxicants, anti-depressants, anti-psychotics, auxiolytics, anti-convulsants, anti-emetics, anti-infectives, anti-histamines, anti-fungal and anti-viral agents, drugs for the treatment of neurological disorders such as Parkinson's disease (dopamine antagonists), drugs for the treatment of alcoholism and other forms of addiction, drugs such as vasodilators for use in the treatment of erectile dysfunction, muscle relaxants, muscle contractants, opioids, stimulants, tranquilizers, antibiotics such as macrolides, aminoglycosides, fluoroquinolones and beta-lactams, vaccines, cytokines, growth factors, hormonal agents including contraceptives, sympathomimetics, diuretics, lipid regulating agents, antiandrogenic agents, antiparasitics, anticoagulants, neoplastics, antineoplastics, hypoglycemics, nutritional agents and supplements, growth supplements, antienteritis agents, vaccines, antibodies, diagnostic agents, and contrasting agents and mixtures of the above (for example the asthma combination treatment containing both steroid and beta-agonist).

The active agent may fall into one of a number of structural classes, including but not limited to small molecules (including insoluble small molecules), peptides, polypeptides, proteins, polysaccharides, steroids, nucleotides, oligonucleotides, polynucleotides, fats, electrolytes, and the like. Specific examples include the beta-2-agonists salbutamol (e.g. salbutamol sulphate) and salmeterol (e.g. salmeterol xinafoate), the steroids budesonide and fluticasone (e.g. fluticasone propionate), the cardiac glycoside digoxin, the alkaloid anti-migraine drug dihydroergotamine mesylate and other alkaloid ergotamines, the alkaloid bromocriptine used in the treatment of Parkinson's disease, sumatriptan, rizatriptan, naratriptan, frovatriptan, almotriptan, zolmatriptan, morphine and the morphine analogue fentanyl (e.g. fentanyl citrate), glibenclamide (a sulphonyl urea), benzodiazepines such as vallium, triazolam, alprazolam, midazolam and clonazepam (typically used as hypnotics, for example to treat insomnia or panic attacks), the anti-psychotic agent risperidone, apomorphine for use in the treatment of erectile dysfunction, the anti-infective amphotericin B, the antibiotics tobramycin, ciprofloxacin and moxifloxacin, nicotine, testosterone, the anti-cholenergic bronchodilator ipratropium bromide, the bronchodilator formoterol, monoclonal antibodies and the proteins LHRH, insulin, human growth hormone, calcitonin, interferon (e.g. beta- or gamma-interferon), EPO and Factor VIII, as well as in each case pharmaceutically acceptable salts, esters, analogues and derivatives (for instance prodrug forms) thereof.

Additional examples of potentially suitable active agents include but are not limited to aspariginase, amdoxovir (DAPD), antide, becaplermin, calcitonins, cyanovirin, denileukin diftitox, erythropoietin (EPO), EPO agonists, domase alpha, erythropoiesis stimulating protein (NESP), coagulation factors such as Factor VIIa, Factor VIII, Factor IX, von Willebrand factor; ceredase, cerezyme, alpha-glucosidase, collagen, cyclosporin, alpha defensins, beta defensins, exedin-4, granulocyte colony stimulating factor (GCSF), thrombopoietin (TPO), alpha-1 proteinase inhibitor, elcatonin, granulocyte macrophage colony stimulating factor (GMCSF), fibrinogen, filgrastim, growth hormones, growth hormone releasing hormone (GHRH), GRO-beta, GRO-beta antibody, bone morphogenic proteins such as bone morphogenic protein-2, bone morphogenic protein-6, OP-1; acidic fibroblast growth factor, basic fibroblast growth factor, CD-40 ligand, heparin, human serum albumin, low molecular weight heparin (LMWH), interferons such as interferon alpha, interferon beta, interferon gamma, interferon omega, interferon tau; interleukins and interleukin receptors such as interleukin-1 receptor, interleukin-2, interluekin-2 fusion proteins, interleukin-1 receptor antagonist, interleukin-3, interleukin-4, interleukin-4 receptor, interleukin-6, interleukin-8, interleukin-12, interleukin-13 receptor, interleukin-17 receptor; lactoferrin and lactoferrin fragments, luteinizing hormone releasing hormone (LHRH), insulin, pro-insulin, insulin analogues, amylin, C-peptide, somatostatin, somatostatin analogs including octreotide, vasopressin, follicle stimulating hormone (FSH), influenza vaccine, insulin-like growth factor (IGF), insulintropin, macrophage colony stimulating factor (M-CSF), plasminogen activators such as alteplase, urokinase, reteplase, streptokinase, pamiteplase, lanoteplase, and teneteplase; nerve growth factor (NGF), osteoprotegerin, platelet-derived growth factor, tissue growth factors, transforming growth factor-1, vascular endothelial growth factor, leukemia inhibiting factor, keratinocyte growth factor (KGF), glial growth factor (GGF), T Cell receptors, CD molecules/antigens, tumor necrosis factor (TNF), monocyte chemoattractant protein-1 endothelial growth factors, parathyroid hormone (PTH), glucagon-like peptide, somatotropin, thymosin alpha 1, thymosin alpha 1 IIb/IIIa inhibitor, thymosin beta 10, thymosin beta 9, thymosin beta 4, alpha-1 antitrypsin, phosphodiesterase (PDE) compounds, VLA-4 (very late antigen-4), VLA-4 inhibitors, bisphosponates, respiratory syncytial virus antibody, cystic fibrosis transmembrane regulator (CFTR) gene, deoxyreibonuclease (Dnase), bactericidal/permeability increasing protein (BPI), and anti-CMV antibody. Exemplary monoclonal antibodies include etanercept (a dimeric fusion protein consisting of the extracellular ligand-binding portion of the human 75 kD TNF receptor linked to the Fc portion of IgG1), abciximab, afeliomomab, basiliximab, daclizumab, infliximab, ibritumomab tiuexetan, mitumomab, muromonab-CD3, iodine 131 tositumomab conjugate, olizumab, rituximab, and trastuzumab (herceptin), amifostine, amiodarone, aminoglutethimide, amsacrine, anagrelide, anastrozole, asparaginase, anthracyclines, bexarotene, bicalutamide, bleomycin, buserelin, busulfan, cabergoline, capecitabine, carboplatin, carmustine, chlorambucin, cisplatin, cladribine, clodronate, cyclophosphamide, cyproterone, cytarabine, camptothecins, 13-cis retinoic acid, all transretinoic acid; dacarbazine, dactinomycin, daunorubicin, dexamethasone, diclofenac, diethylstilbestrol, docetaxel, doxorubicin, epirubicin, estramustine, etoposide, exemestane, fexofenadine, fludarabine, fludrocortisone, fluorouracil, fluoxymesterone, flutamide, gemcitabine, epinephrine, L-Dopa, hydroxyurea, idarubicin, ifosfamide, imatinib, irinotecan, itraconazole, goserelin, letrozole, leucovorin, levamisole, lomustine, mechlorethamine, medroxyprogesterone, megestrol, melphalan, mercaptopurine, methotrexate, metoclopramide, mitomycin, mitotane, mitoxantrone, naloxone, nicotine, nilutamide, octreotide, oxaliplatin, pamidronate, pentostatin, pilcamycin, porfimer, prednisone, procarbazine, prochlorperazine, ondansetron, raltitrexed, sirolimus, streptozocin, tacrolimus, tamoxifen, temozolomide, teniposide, testosterone, tetrahydrocannabinol, thalidomide, thioguanine, thiotepa, topotecan, tretinoin, valrubicin, vinblastine; vincristine, vindesine, vinorelbine, dolasetron, granisetron; formoterol, fluticasone, leuprolide, midazolam, alprazolam, amphotericin B, podophylotoxins, nucleoside antivirals, aroyl hydrazones, sumatriptan; macrolides such as erythromycin, oleandomycin, troleandomycin, roxithromycin, clarithromycin, davercin, azithromycin, flurithromycin, dirithromycin, josamycin, spiromycin, midecamycin, leucomycin, miocamycin, rokitamycin, andazithromycin, and swinolide A; fluoroquinolones such as ciprofloxacin, ofloxacin, levofloxacin, trovafloxacin, alatrofloxacin, moxifloxicin, norfloxacin, enoxacin, grepafloxacin, gatifloxacin, lomefloxacin, sparfloxacin, temafloxacin, pefloxacin, amifloxacin, fleroxacin, tosufloxacin, prulifloxacin, irloxacin, pazufloxacin, clinafloxacin, and sitafloxacin; aminoglycosides such as gentamicin, netilmicin, paramecin, tobramycin, amikacin, kanamycin, neomycin, and streptomycin, vancomycin, teicoplanin, rampolanin, mideplanin, colistin, daptomycin, gramicidin, colistimethate; polymixins such as polymixin B, capreomycin, bacitracin, penems; penicillins including penicllinase-sensitive agents like penicillin G, penicillin V; penicllinase-resistant agents like methicillin, oxacillin, cloxacillin, dicloxacillin, floxacillin, nafcillin; gram negative microorganism active agents like ampicillin, amoxicillin, and hetacillin, cillin, and galampicillin; antipseudomonal penicillins like carbenicillin, ticarcillin, azlocillin, mezlocillin, and piperacillin; cephalosporins like cefpodoxime, cefprozil, ceftbuten, ceftizoxime, ceftriaxone, cephalothin, cephapirin, cephalexin, cephradrine, cefoxitin, cefamandole, cefazolin, cephaloridine, cefaclor, cefadroxil, cephaloglycin, cefuroxime, ceforanide, cefotaxime, cefatrizine, cephacetrile, cefepime, cefixime, cefonicid, cefoperazone, cefotetan, cefmetazole, ceftazidime, loracarbef, and moxalactam, monobactams like aztreonam; and carbapenems such as imipenem, meropenem, pentamidine isethiouate, albuterol sulfate; lidocaine, metaproterenol sulfate, beclomethasone diprepionate, triamcinolone acetamide, budesonide acetonide, fluticasone, ipratropium bromide, flunisolide, cromolyn sodium, and ergotamine tartrate; taxanes such as paclitaxel; SN-38; tyrphostines.

Other agents that may be used include: Linezolid; Treprostinol optionally in combination with a PDE5 Inhibitor; Oxyntomodulin; and Palonosetron optionally in combination with a, preferably high potency, NK1 antagonist.

It will be understood that the above exemplary active agents are meant to encompass, as applicable, analogues, agonists, antagonists, inhibitors, isomers, and pharmaceutically acceptable salt forms thereof. In regard to peptides and proteins, the invention is intended to encompass synthetic, recombinant, native, glycosylated, non-glycosylated, and biologically active fragments and analogues thereof.

In some preferred embodiments, the dry powder may include one or more active agents selected from adrenaline, glucose, glucagon, naloxone, insulin or the like. In one example, the dry powder includes microparticles, nanoparticles, microcapsules, nanocapsules, microspheres, and/or nanospheres of adrenaline and/or atropine for the treatment of cardiac failure, cardiac dysfunction, cardiac arrest, anaphylaxis, drug overdose or the like.

In another example, the dry powder includes particulate glucose and/or glucagon for the treatment of hypoglycaemia, diabetes induced coma or the like.

In another example, the dry powder includes particulate naloxone for the treatment of opioid overdose.

In another example, the dry powder includes particulate benzodiazepine, phenytoin or anti-seizure medications for the treatment of seizure.

Accordingly, the delivery device 100 can be used to deliver dry powder to a biological subject by generating a gas flow, entraining a dose of dry powder in the gas flow and delivering the gas flow including the entrained dry powder to the subject's airway. It will be appreciated that the gas flow may deliver dry powder into the subject's lungs without requiring the subject to inhale. Alternatively, if the subject is conscious, the subject may inhale the medicament themselves by inhaling at the outlet 104. This may be done, for example, if the subject has anaphylaxis and the like where it has been shown that early administration of adrenaline can significantly improve subject outcome.

The above features of delivery device 100, including the ability of the device to be used to deliver dry powder to a subject without requiring the subject to inhale, offer a number of significant advantages.

In particular, the delivery device 100 is adapted to allow first responders to deliver potentially life-saving medicament to a subject. This immediate delivery can significantly improve not only the survival, but the functional outcome of a subject. For example, for subjects with cardiac dysfunction, the ability to more rapidly administer adrenaline, particularly when compared with traditional methods such as intravenous administration, significantly increases return of spontaneous circulation, survival rates and decreases the risk of severe post-resuscitation disability.

Similarly in the case of hypoglycaemia and diabetes induced comas, it is important to deliver glucose or glucagon as quickly as possible. This often is not possible orally as the subject may be unconscious rendering them unable to swallow. Furthermore, the subject is often unable to inhale, meaning delivery of the medicament by the respiratory system by an alternative method, for example by positive pressure air, is required.

Similarly in the case of opioid overdose, it is important to deliver naloxone as quickly as possible to prevent death. This is not always possible since opioid abusers have very difficult veins to access, and there is risk of needle stick injury.

Similarly in the case of seizure, it is important to deliver benzodiazepine or phenytoin as quickly as possible to prevent the patient from self-harm. This is both difficult and dangerous to do with a drip, e.g. if the patient is fitting. Locating a vein may be difficult which increases the risk of a needle stick injury. The delivery device 100 allows for immediate dosage of the drug to reduce or stop seizure and allow for intravenous insertion in relative safety.

Figure 32:
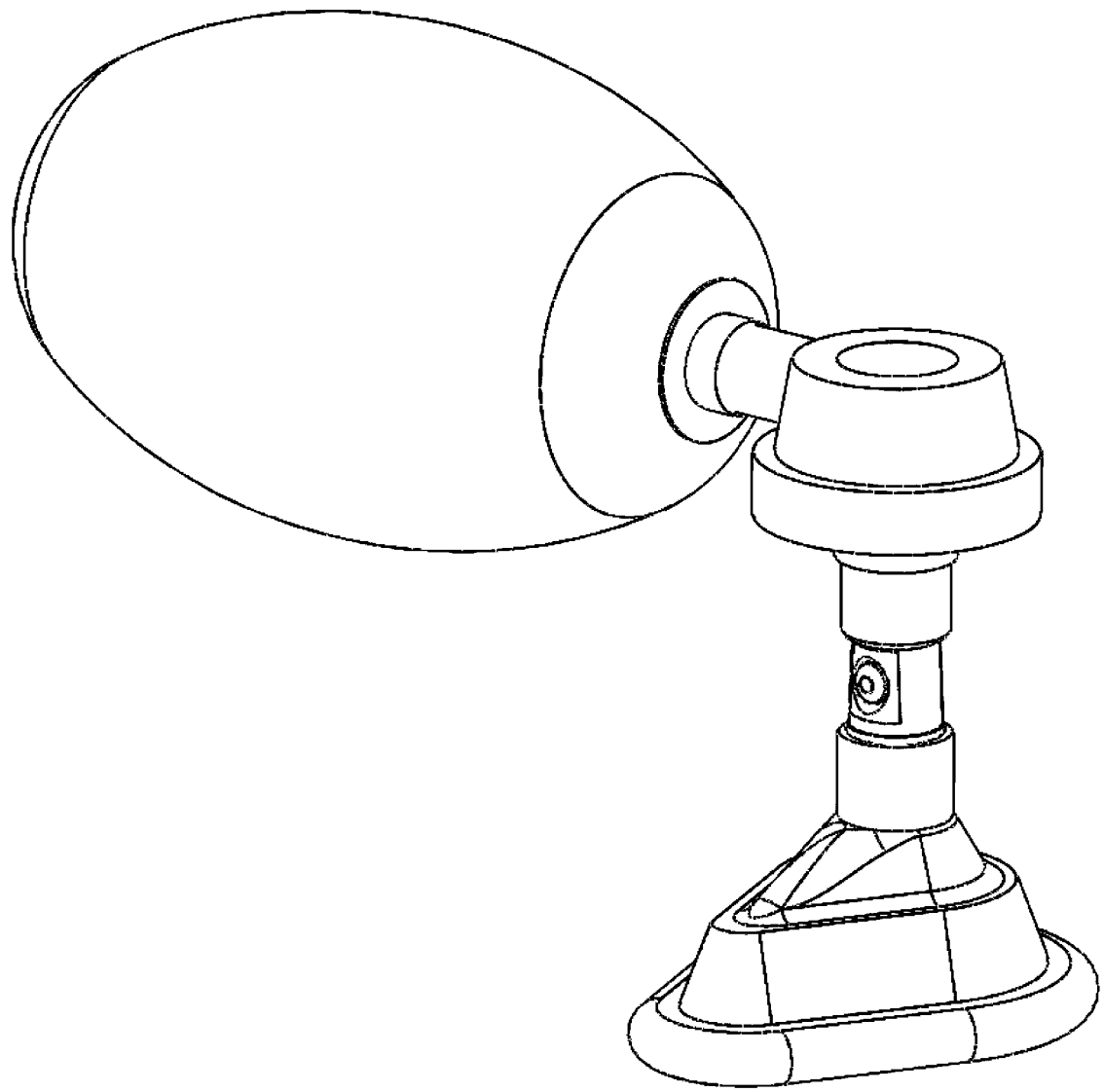
FIG. 32 shows an embodiment of the delivery device connected to a Bag Valve Mask.

The administration of a dry powder to a subject's airway using the delivery device 100 also eliminates or offsets the need to use large, complex, and expensive nebulising equipment for aerosolising any liquid medicaments. Such equipment is typically only available in hospitals and specialised medical premises and requires trained personnel to setup and operate. In contrast, the delivery device 100 is sufficiently light-weight, portable, and inexpensive to be made available for use in many environments, such as homes, shopping centres, offices, and the like. Furthermore, the delivery device 100 may be used with any supply of positive pressure gas as discussed above, such as from a Bag-Valve-Mask (BVM) (e.g. Ambu-bag), resuscitation bag, pressurized gas canister, mouthpiece, or simply an operator exhaling, further increasing its portability and usability.

Additionally, in this arrangement a caregiver or administrator may use the delivery device 100 with little or no specialised training. In this regard, the delivery device 100 could be made widely available and be readily used in a similar fashion to and in environments like those where automated electronic defibrillators are stored.

As a consequence, by way of example, this allows adrenaline to be delivered as part of a CPR procedure, resulting in significantly improved subject outcomes. For example, for subjects in cardiac arrest, heart failure or anaphylaxis, where the subject is not located in a hospital or specialised medical centre, the ability to have particulate adrenaline available and readily administered using the delivery device 100 during the initial stages of the condition could have a significant impact on the subject's post-resuscitation outcomes and quality of life, as discussed above. In this regard, as it is crucial to administer CPR and adrenaline immediately in the event of a cardiac arrest, the immediate availability, simplicity and portability of the delivery device 100 increases probability of survival and decreases the risk of severe disability post-resuscitation.

Further, the use of positive pressure gas is particularly beneficial where a subject is unresponsive, unconscious, or the like, which is typically the case for subjects with hypoglycaemia, heart failure, or in cardiac arrest. In this regard, the delivery device 100 does not rely on the subject's ability to inhale, or otherwise respond, in order to administer the medicament to the subject's airways and alveoli. Rather, the positive pressure gas entrains and pushes the dry powder into the airways where it is absorbed into the blood stream. Thus, the delivery device 100 is suitable for the treatment of cardiac arrest with adrenaline, and in one example, the delivery device 100 may be used during administration of CPR.

A number of further exemplary features of embodiments of the delivery device 100 will now be described.

Typically, dry powder inhalers have a high variation in dosage due to incorrect use. The device 100 has built-in features to assist in correct usage and facilitate standardisation in dosage of drug delivered to the patient.

One such feature is that the resonance between gas pressure waves and the cantilever structure 140 may generate a sound that can be heard by the user, providing audible feedback 1200 to communicate that the device 100 is operating correctly, as set out in FIG. 12.

Furthermore, in particular regard to the embodiment in which the dose of dry powder is stored in indentations on the cantilever structure 140, the cantilever structure itself is preferably adapted such that powder is only substantially released by striking the deagglomerating surface, when airflow is sufficient for administration 1510.

Another such feature is that if the caregiver is blowing or otherwise administering gas too fast through the device, the cantilever 140 can seal against the deagglomerating surface 150, restricting gas flow through the device 100. It should be noted that the device 100 will continue to ventilate in this condition.

It should also be noted that, in some embodiments, for example as depicted in FIG. 11, the device 100 can comprise a valve 400, to release or relieve pressure. Preferably, the valve functions to release pressure at between about 1 kPa and 15 kPa, including about: 2, 3, 4, 5, 6, 7, 8, 9, 10, 11, 12, 13, and 14 kPa; more preferably at between 3 kPa and 10 kPa; and even more preferably at about 6 kPa.

In some embodiments, after passing through the slots 152 in or of the deagglomerating surface 150, the dry powder is further deagglomerated prior to delivery to a patient. In one example, the device housing 110 further includes an eddy generating structure 160, such as shown in FIGS. 10B and 10C, disposed downstream of the deagglomerating surface 150. The eddy generating structure 160 is adapted to generate small, high energy eddies that promote further deagglomeration of the entrained dry powder as a result of fluid turbulence.

Accordingly, an eddy generating structure 160 may be inserted into the device housing 110 (typically during assembly of the device) so as to be downstream of the deagglomerating surface 150. In one example, the eddy generating structure 160 comprises an one or more, fixed elongate members 162, as shown in FIG. 5B-10B. The elongate members 162 may be in the form of an array of spaced apart and parallel said members. Typically, the members are disposed beneath the deagglomerating surface 150 in abutment therewith. The fixed elongate members 162 typically extend the length of the deagglomerating surface 150 and are aligned with one or more respective slots 152 in the surface 150 to ensure that the entrained dry powder is forced to flow around the fixed members 162. In one example, the fixed members 162 are round bars secured to the device housing 110.

This arrangement of elongate members 162 can serve to maximize the turbulence generated through this section of the device 100. This turbulence is typically in the form of small eddies of high energy, such that the medicament aggregates can be further deaggregated by fluid turbulence. By arranging the fixed members 162 in a staggered arrangement, vortex shedding is promoted which generates the highest number of high energy eddies. A further advantage of the eddy generating structure 160 is that by increasing the gas velocity, particles are more likely to become entrained in the gas flow.

Preparatory steps can be performed to ensure that the delivery device 100 is ready for use. In one example, the outlet 104 of the device 100 may be inserted into an inlet of a universal mask, while the outlet of a resuscitation bag (e.g. Ambu-bag) may be inserted into the inlet 102 of the device 100, such as depicted in FIG. 32. Gas flow through the device 100 between the inlet 102 and outlet 104 may then be initiated to ensure effective flow rates and carried on until drug delivery is necessary. Drug delivery can then be provided, for example upon depression of the container 300, when desired.

It is to be further appreciated that the ability to provide non-medicated breaths is an important feature when using advanced airways such as an endotracheal tube and supraglottic airways. For example, a caregiver can confirm that the advanced airway has been inserted correctly by providing non-medicated breaths and watching the chest cavity rise. This can help to ensure that the medicament dose will be delivered to the lungs only when required.

The delivery device 100 may further comprise one or more adapters. In this regard, an inlet adaptor may be coupled to the delivery device 100 and in fluid communication with the inlet 102 and/or an outlet adaptor may be coupled to the delivery device 100 and in fluid communication with the outlet 104. The inlet adaptor may be for coupling the apparatus 100 to one or more of a Bag-Valve-Mask (BVM) (e.g Ambu-bag), a resuscitation bag, a ventilator, an oxygen pump, a compressed gas supply, a manual resuscitator, an automatic resuscitator, a mouthpiece, or the like. Additionally, or alternatively, the outlet adaptor may be for coupling the delivery device 100 to a mask, advanced airway (e.g. endotracheal tube), supraglottic airway (e.g. laryngeal airway), or the like. However, this is not essential and in other examples the delivery device 100 may be directly coupled and/or permanently attached to any of the above components without the use of an inlet and/or outlet adapter. Alternatively, the outlet 104 can incorporate a mouthpiece allowing it to be placed directly into the subject's mouth.

In particular, the inlet and/or outlet adapter may comprise a universal adapter or universal connector. This is particularly beneficial as it allows the delivery device 100 to be provided with one or more universal adapters already attached. In this regard, in use the operator may quickly and easily select the most appropriate positive pressure gas supply to be coupled to the delivery device 100 via the universal inlet adapter. Additionally or alternatively, the operator may select the most appropriate device to be coupled to the apparatus via the universal outlet adapter. The operator's selection will typically depend upon the circumstances, surroundings, subject's condition, and the like. For example, in a home or non-hospital setting, the positive pressure gas may simply be supplied via the operator's exhalation, or a BVM, whereas in a hospital setting the operator may have access to a ventilator, or more complex/expensive positive pressure gas supply.

The delivery device 100 may also comprise one or more backflow mechanisms, such as exhalation valves, one-way valves, seals, or the like, to prevent the dry powder and/or bodily fluids from being transferred out of the apparatus through the inlet 102 and to an operator (for example). The backflow mechanism(s) are adapted to prevent or at least constrain the flow of powder out of the inlet 102, which could then be transferred to the operator, for example, in the event the subject's exhalation is providing the positive pressure gas to the delivery device 100. In addition, the backflow mechanism(s) may ensure that substantially the entire dose is administered to the subject's airway, and is not dissipated or lost, for example, to the external environment.

Backflow mechanisms may also be included, for example, to prevent a caregiver or administrator from inhaling any of the subject's exhalation.

Alternatively, the backflow mechanism(s) may be an externally placed exhalation valve, placed on the inlet 102 between the device 100 and the positive pressure gas supply, or between the outlet 104 and the inlet of the universal mask or advanced airway.

In embodiments wherein the device 100 comprises the container 300, the device may comprise a mechanism that prevents the container 300 from being depressed before the Bag-Valve-Mask, resuscitation bag or the positive pressure gas supply is attached to the inlet 102 of the device. Preferably this could be an additional component in the form of a flow- or fitting-operated latch.

In embodiments wherein the device 100 comprises the container 300, the device may comprise an external mechanism or component (not shown) as an alternative to the piercing cup 106, in order to tear and fold the seal 306 of the store 300, which when operated, exposes the powder to the airflow. The external component may be in the form of an external piercing cup, external pin or a plate.

To prevent or limit deposition of the medicament upon a patient's face during use of device 100 with a mask, the device 100 may incorporate an elongated, typically flexible, extension. In this embodiment, the device inlet 102 may be attached to the outlet of a resuscitation bag (e.g. Ambu-bag), the device housing 110, outlet 104 or part thereof may protrude through the inlet of a universal mask and the elongated, flexible extension further protrude into the patients mouth.

It should be noted that when positive pressure air is supplied by exhalation from a caregiver or operator or negative pressure air is supplied through subject inhalation, there may be a degree of variability in the air flow provided through the apparatus. Consequently, a full dosage of the dry powder may not be delivered into the patient's airway and lungs after one breath. In this case, multiple breaths may be used to deliver the full dose of medicament.

Figure 13:
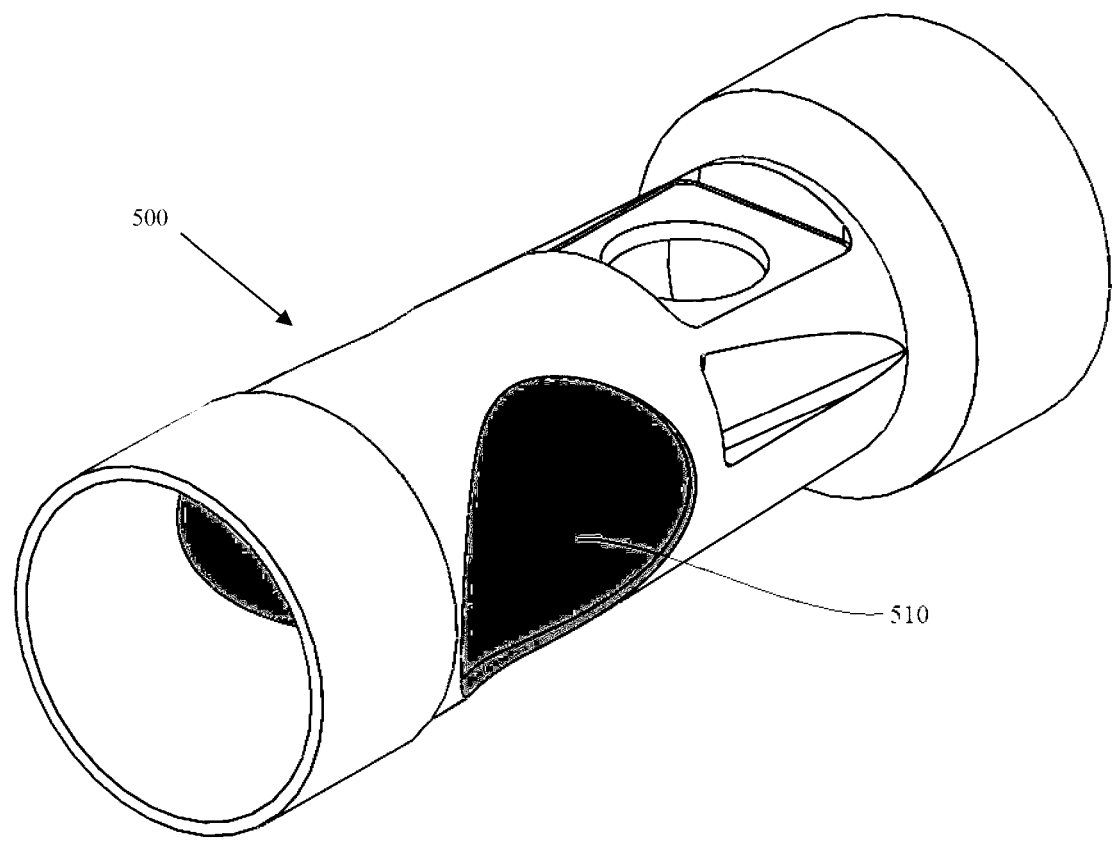
FIG. 13 is a perspective view of an exemplary delivery device with compliant membranes covering windows.

In some embodiments, an acoustic isolator 500 can be incorporated as an accessory or a part of the housing 110, as shown for example in FIG. 13. The inclusion of the acoustic isolator 500 can be advantageous for adapting the device 100 for use with various types of interfacing equipment such as universal masks and endotracheal tubes of various sizes, to assist with overcoming possible acoustic interaction between the device and interfacing equipment, which may compromise vibration or resonance of the cantilever structure 140. The acoustic isolator 500 can consist of one or more dampening walls 510 that are in contact with the internal gas flow. Typically, the one or more dampening walls 510 will be made from an elastomer or polymer (e.g. thermoplastic), although without limitation thereto. It is preferred that the one or more dampening walls 510 have a loss coefficient ($\eta$; preferably as measured at 30° C.) of less than about of 0.6, including less than about: 0.5, 0.4, 0.3, 0.2, or 0.1. More preferably, the one or more dampening walls 510 have a loss coefficient of less than about 0.4 as measured at 30° C.

It will be further appreciated that, additionally or alternatively to the acoustic isolator 500, other components may be included in the device to dampen acoustic waves, for example one or more of: a sudden expansion; a plenum chamber; a compliance chamber; and an anechoic surface, all of which will be known to those skilled in the art.

Typically, the administered microparticles will have a d50 or Mean Mass Aerodynamic Diameter (MMAD) less than 6

µm. As will be understood by the skilled person 'd50' or 'D50' refers to the value that the particle diameter of 50% by mass of a particulate sample is less than. The d50 particle MMAD is preferably between about 0.5 and about 20 µm, including about: 1, 2, 3, 4, 5, 6, 7, 8, 9, 10, 11, 12, 13, 14, 15, 16, 17, 18, and 19 µm, more preferably between about 0.5 and 10 µm, and even more preferably between 1 and 6 µm, including about: 1.5, 2, 2.5, 3, 3.5, 4, 4.5, 5 and 5.5 µm. The microparticles may be manufactured using any suitable microparticle technique. Alternatively, the particles may be manufactured as microspheres and/or microcapsules, using any suitable microsphere and/or microcapsule technique.

In one particularly preferred example, the delivery device 100 is for administering microparticles containing the active pharmaceutical ingredient adrenaline (epinephrine).

Figure 3:
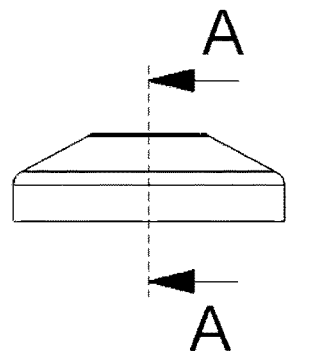
FIG. 3 shows side and section views of an puncturing device of the exemplary container shown in FIG. 4.
Figure 4A:
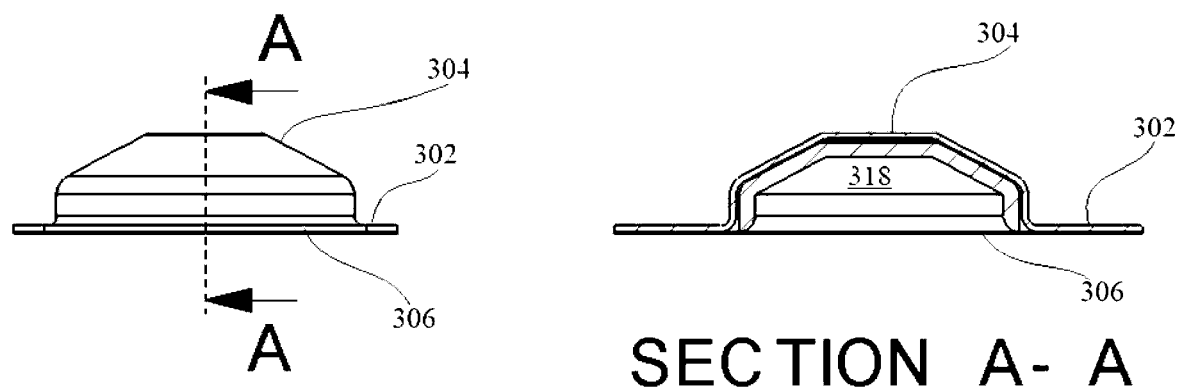
FIG. 4A shows respective front and cross sectional side view of an exemplary container, in the form of a blister unit, for holding a dose of dry powder.
Figure 4B:
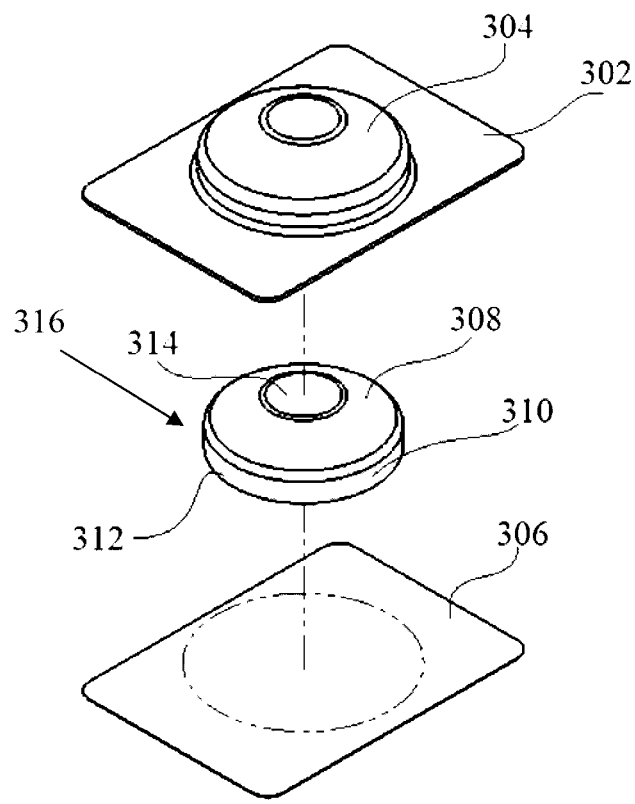
FIG. 4B is an exploded view of the blister unit of FIG. 4A.

Referring now particularly to FIGS. 3 and 4, the container or store 300 is shown in detail and will be described further as follows. As set out above, the container 300 is suitable for use with the delivery device 100, and may form part of said delivery device. However, the container 300 can also be used independent of delivery device 100, and can be useful for any application wherein it is desirable to releasably store a particulate substance or composition. For the sake of clarity, the particulate composition or substance releasably stored within container 300 will preferably be or comprise a dry powder, but is not limited thereto. The particulate composition may include any suitable active agent such as hereinabove described.

The container 300 is typically in the form of blister pack with a shell 304 sealed by a seal 306. While a foil seal is preferred, any suitable material may be used including for example plastic. A particulate substance or composition, such as the dry powder herein described, is or can be, releasably stored within storage volume 318. Suitably, the container 300 protects the dry powder from one or more of moisture, oxidation and photo- or chemical degradation.

The container 300 typically comprises a puncturing device 316 for rupturing the seal 306. Typically, the puncturing device 316 is a ring or cup structure that fits within the shell 304 so as to provide a clearance fit between the puncturing device and the blister shell. The puncturing device 316 comprises a cylindrical wall portion 310 and a top portion 308 which has a tapered profile.

A clearance is typically required to prevent collision between the puncturing device 316 and the device 100 during dispensing of powder, when the container 300 is used with device 100, and/or for correct seal 306 breaking and folding.

In embodiments, the clearance between the outer diameter of the puncturing device 316 and the inner diameter of opening 106 of a corresponding device 100 (or other suitable device) is typically more than the combined error of manufacturing and assembling the device (said errors typically being less than about 10% of device length). This assists with positioning of the puncturing device 316 over the opening, such that there is no substantial collision during dosing.

In use, the shell 304 of the container 300 is depressed by a user which causes the puncturing device 316 to pierce the seal 306 thereby releasing the particulate substance or composition. The shell 304 is designed such that its top preferentially buckles when the blister container 300 is depressed due to a force, which results in the puncturing device 316 to tear and fold the seal 306.

The puncturing device 316 may be attached to the blister shell 304 in order to prevent the puncturing device 316 separating or coming loose from the blister shell 304 upon depression. By way of non-limiting example, the top centre 314 of the puncturing device 316 may be attached to the shell 304 by welding, mechanical fastening, glue or the like.

The inclusion of the puncturing device 316 in container 300 has been determined to be particularly advantageous as it provides a rigid structure within the container 300 to assist in breaking the seal 306. It will be appreciated that the seal 306 is not easily broken by depression in the absence of the puncturing device 316, as the dry powder will simply compress. This contrasts with stores for containing a solid component e.g. a pill, wherein a force onto the seal strong enough to rupture the seal can be achieved when the blister is depressed, via the solid component.

It will be appreciated that the blister shell 304 is typically made from a material having less rigidity than the puncturing device 316. By way of non-limiting example, the blister shell 304 may be formed from cold-formed foil laminate while the puncturing device 316 is formed from a polymer with higher rigidity than the blister. Alternatively, the puncturing device 316 and blister shell 304 may also be formed from a similar cold-formed foil laminate or polymer composition, however with puncturing device 316 comprising higher rigidity than the blister shell 304.

Further detail regarding particularly preferred examples of the delivery device 100, and use thereof, shall now be provided as follows.

Figure 1B:
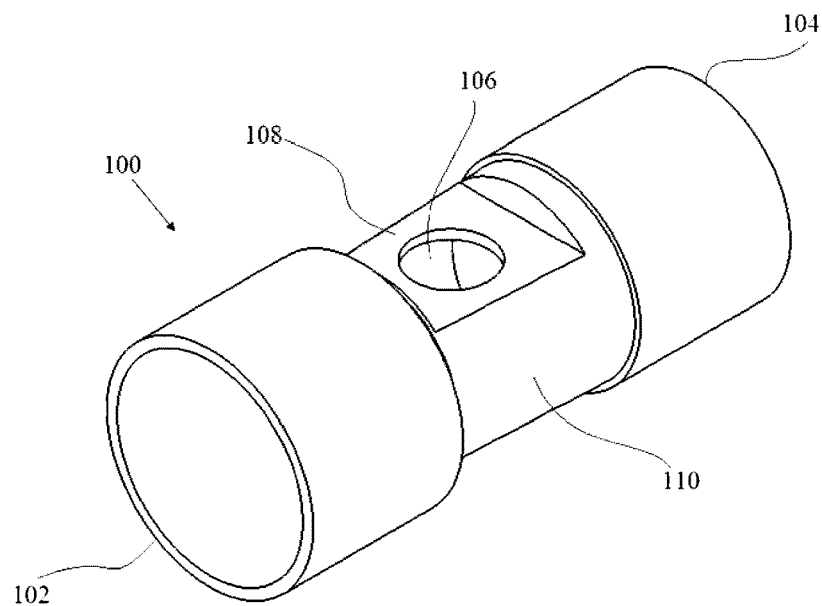
FIG. 1B shows the delivery device of FIG. 1A with the container and the collar removed.
Figure 2A:
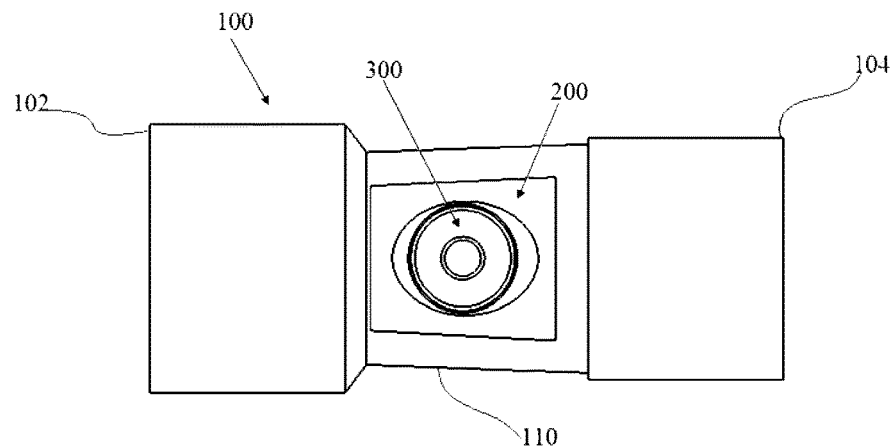
FIG. 2A shows a top view of the delivery device of FIG. 1A.
Figure 2B:
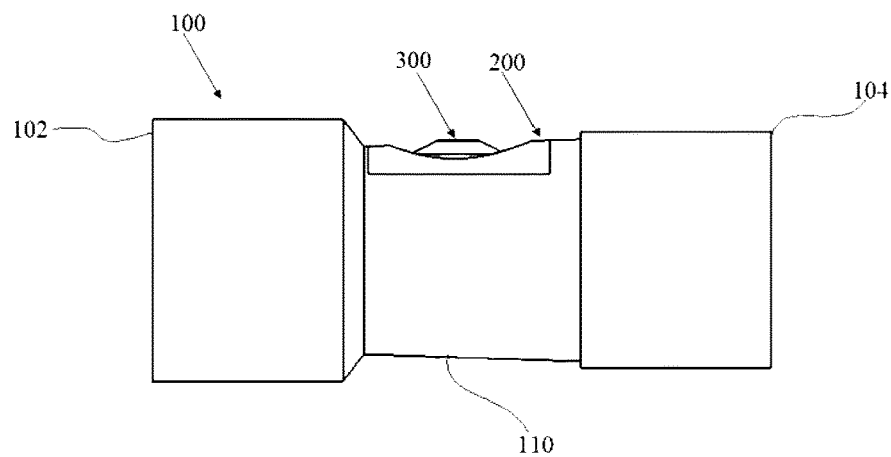
FIG. 2B shows a side view of the delivery device of FIG. 1A.

As shown in FIG. 1B, the housing 110 of the delivery device 100 has an opening 106 disposed part way between the inlet and outlet of the device which is covered by the container 300. Opening 106 further provides a passage for the dry powder to enter the housing 110 after it has been released from the container 300.

In use, similar as described above, a user depresses the shell 304 of the store 300 which actuates the puncturing device 316, urging it downwards into contact with the seal 306. The puncturing device 316 then ruptures the seal 306 which releases the dose of dry powder from the container 300 into the device housing 110, for example into a space or region 115 above the cantilever structure 140.

It will be further appreciated that, as described herein, release of a dry powder can alternatively occur in response to vibration or resonance of the cantilever structure 140 as described below, wherein the dry powder is located in or on the cantilever structure 140, such as in a plurality of indentations as shown in FIG. 14.

Figure 6A:
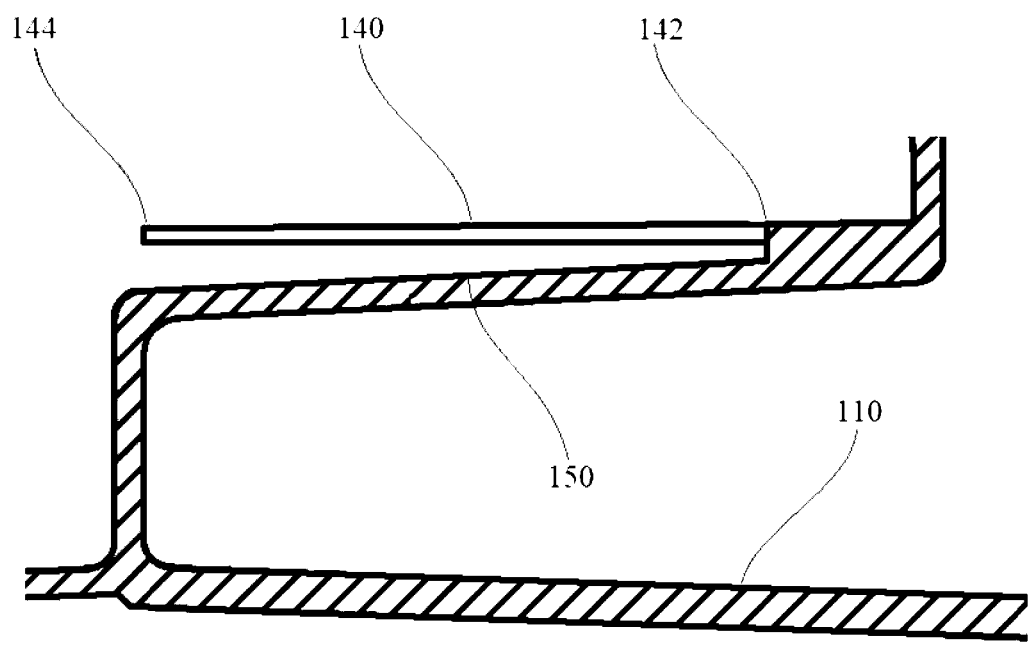
FIG. 6A is a cross sectional side view of an exemplary cantilever structure in the form of a reed, in an undeflected position such as when there is no gas flow through the device.
Figure 6B:
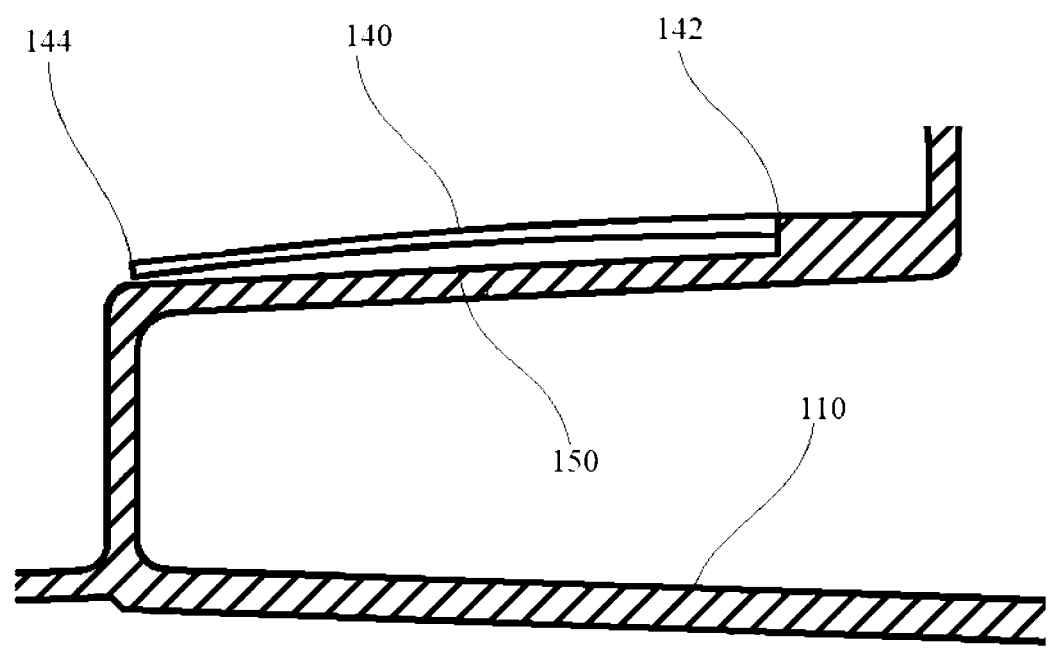
FIG. 6B is a cross sectional side view of the reed of FIG. 6A, in a deflected position such as when gas flow through the device induces forced vibration thereof.
Figure 7A:
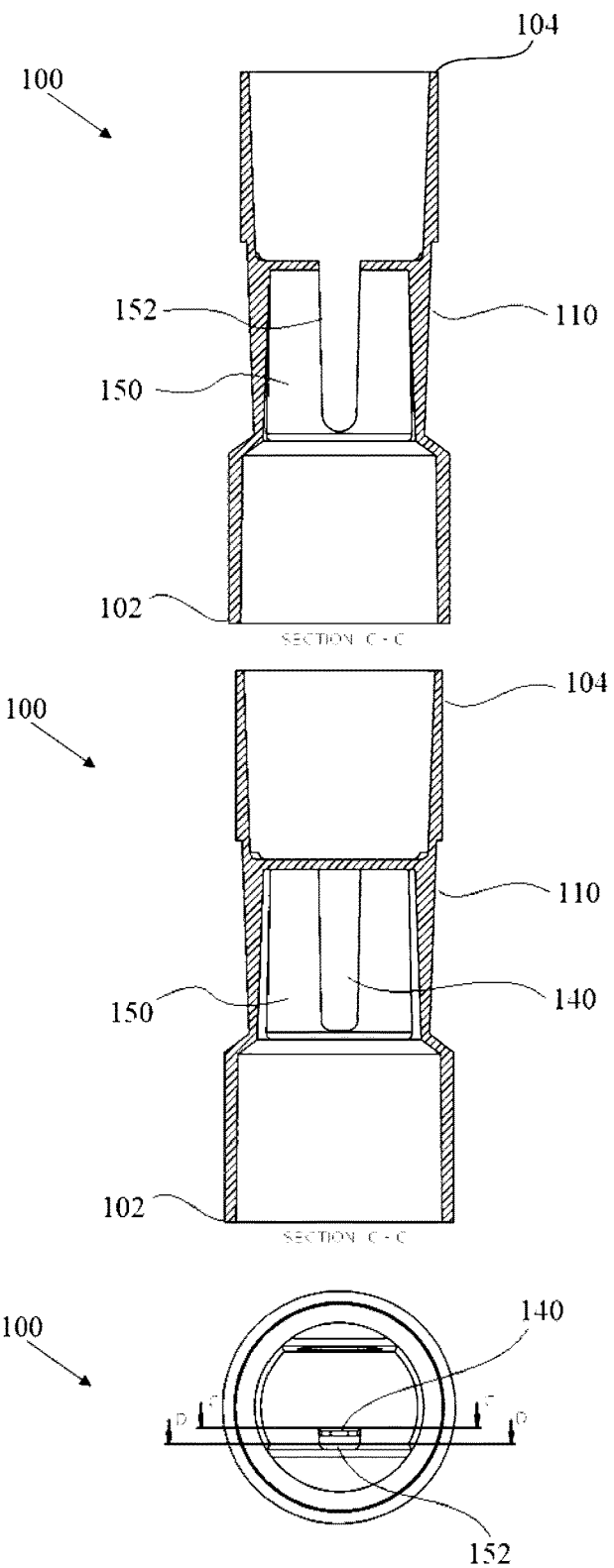
FIG. 7A shows respective cross sectional views and a front view of the delivery device of FIG. 5A with a single reed and single slot, and without a fixed member eddy generator.
Figure 7B:
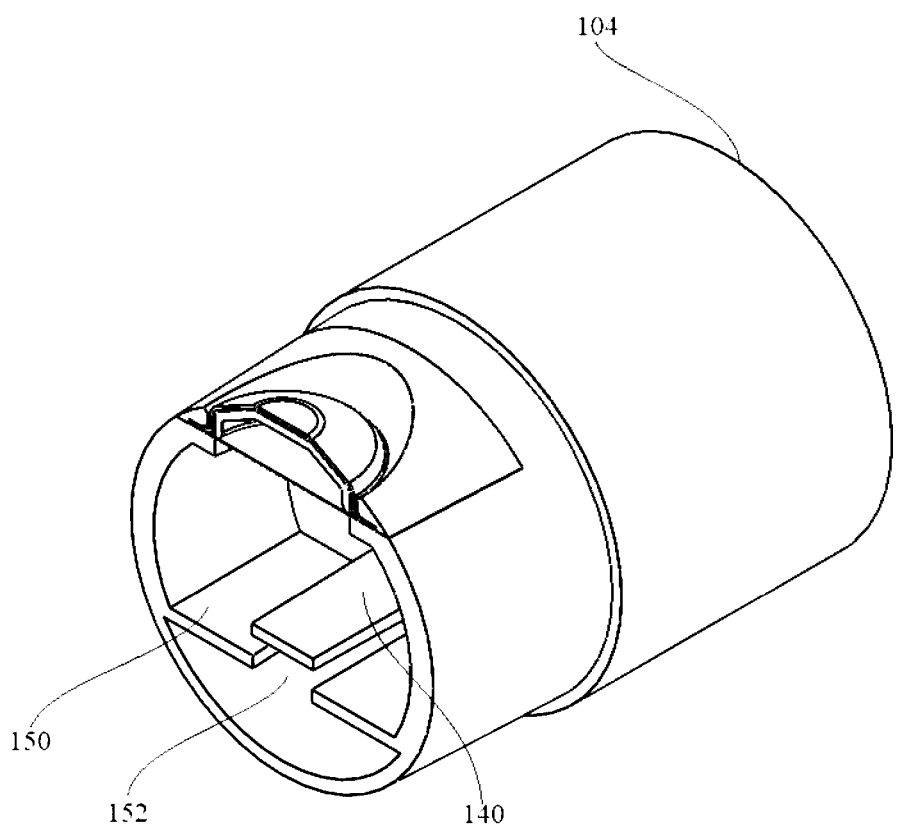
FIG. 7B shows a cross sectional perspective view of the delivery device of FIG. 5A.

As gas flow into the device 100 is initiated, the cantilever structure 140, in the form of one or more reeds, preferably a single reed, begins to vibrate in the space or region 115 at a modal frequency. As shown in FIG. 6A, the reed 140 has a cantilever structure having a fixed end 142 and a free end 144. When there is no gas flow through the housing, the reed 140 remains in an undeflected position. Gas flow through the housing 110 however causes the reed 140 to undergo forced vibration in which it oscillates between deflected positions. In the deflected position shown in FIG. 6B, the free end 144 of the reed 140 is urged towards the deagglomerating surface 150. Aggregates of dry powder that are between the deagglomerating surface 150 and the reeds 140 will be deagglomerated and/or crushed or milled to a finer aggregate or particle size.

The deagglomerating surface 150 comprises a filter, which is preferably a single slot as shown by FIGS. 7A, 7B, 8A and 8B but may alternatively be a plurality of slots 152 as shown in FIGS. 9A, 9B, 10A and 10B. The one or more slots extend lengthwise in substantially the same direction as the reed 140. It is to be appreciated, however, that the filter may take any suitable form including for examples a wire mesh or plurality of holes. When the aggregates of dry powder have been deagglomerated to a certain size they will pass through the filter (in this example slot(s) 152) and enter the next stage of the device 100.

Figure 8A:
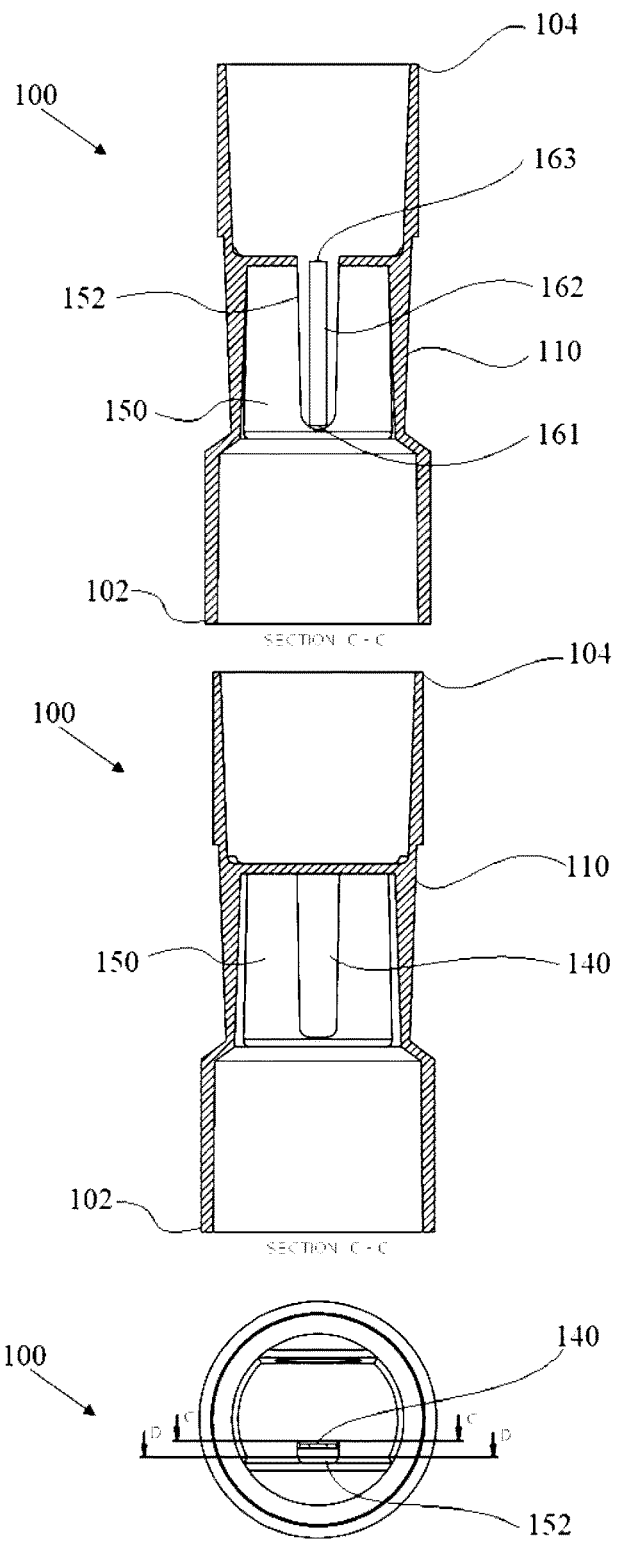
FIG. 8A shows respective cross sectional views and a front view of the delivery device of FIG. 5B with a single reed, single slot, and a single fixed member eddy generator.
Figure 8B:
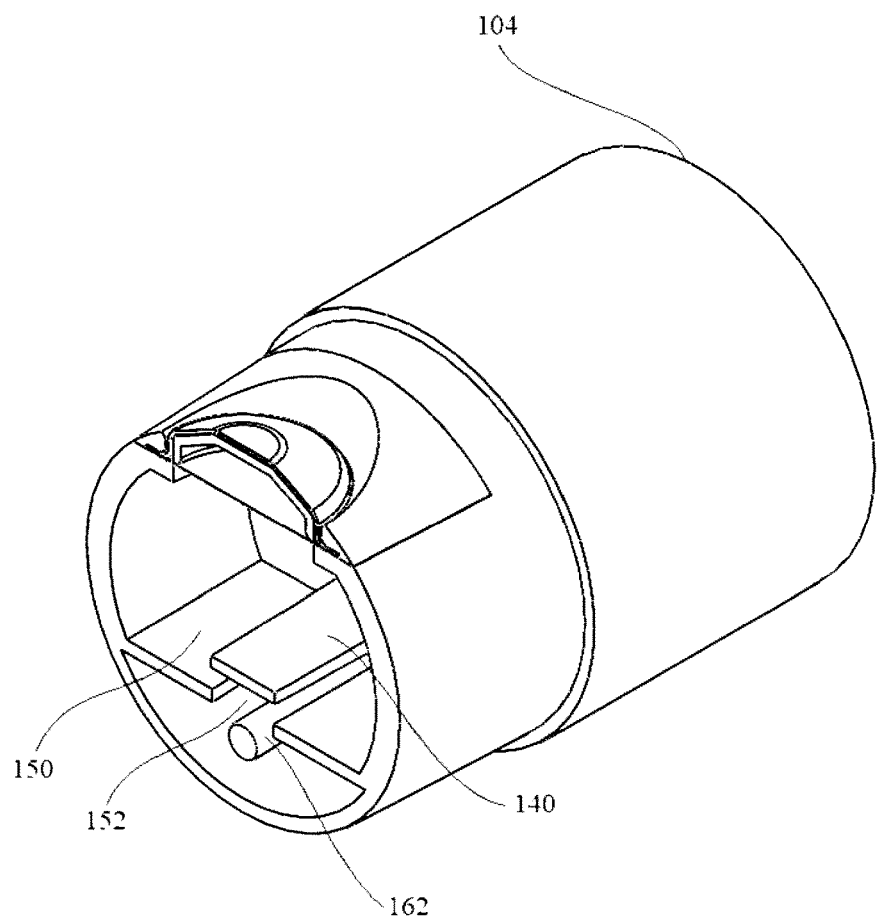
FIG. 8B shows a cross sectional perspective view of the delivery device of FIG. 5B.
Figure 9A:
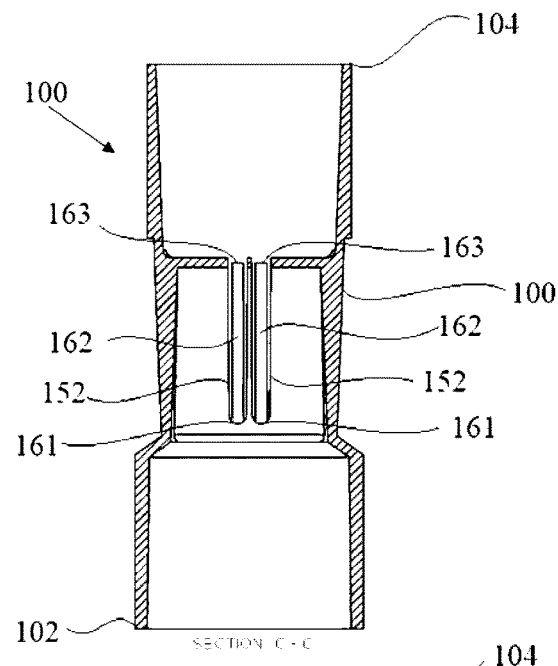
FIG. 9A shows respective cross sectional views and a front view of a delivery device configuration with a single reed, two slots and two fixed member eddy generators.
Figure 9A:
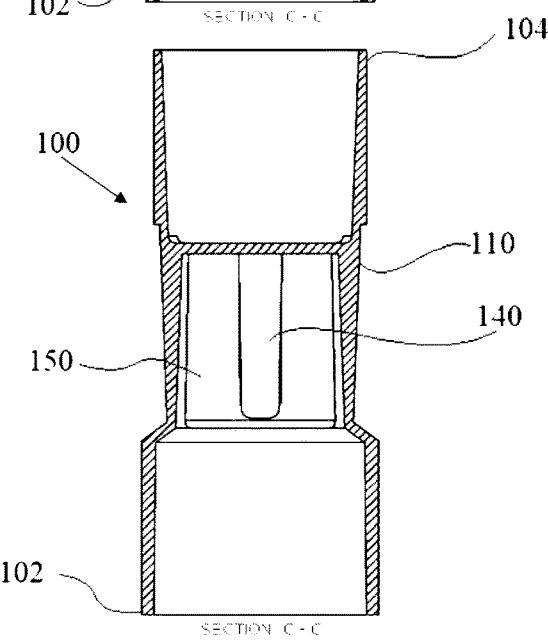
Figure 9A:
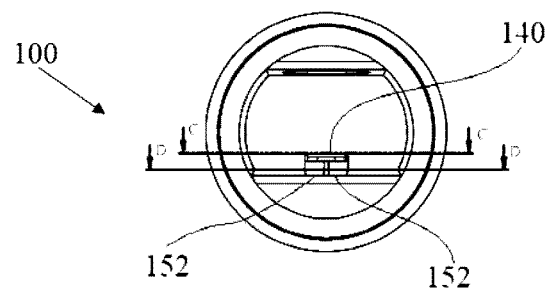
Figure 9B:
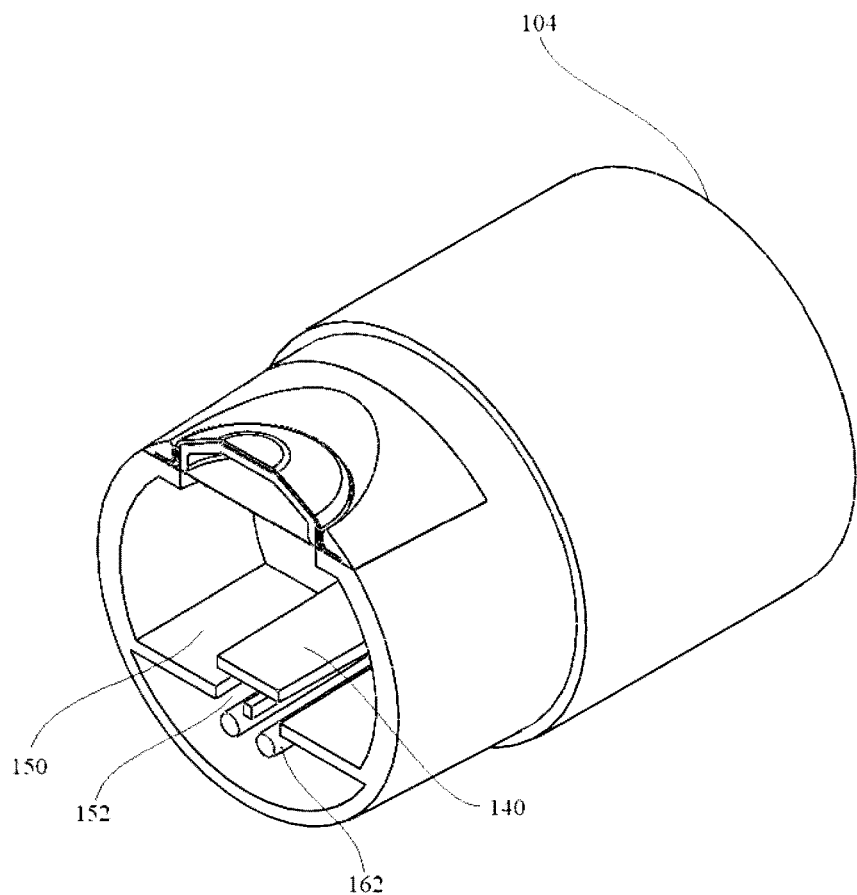
FIG. 9B shows a cross sectional perspective view of the delivery device of FIG. 9A.
Figure 10A:
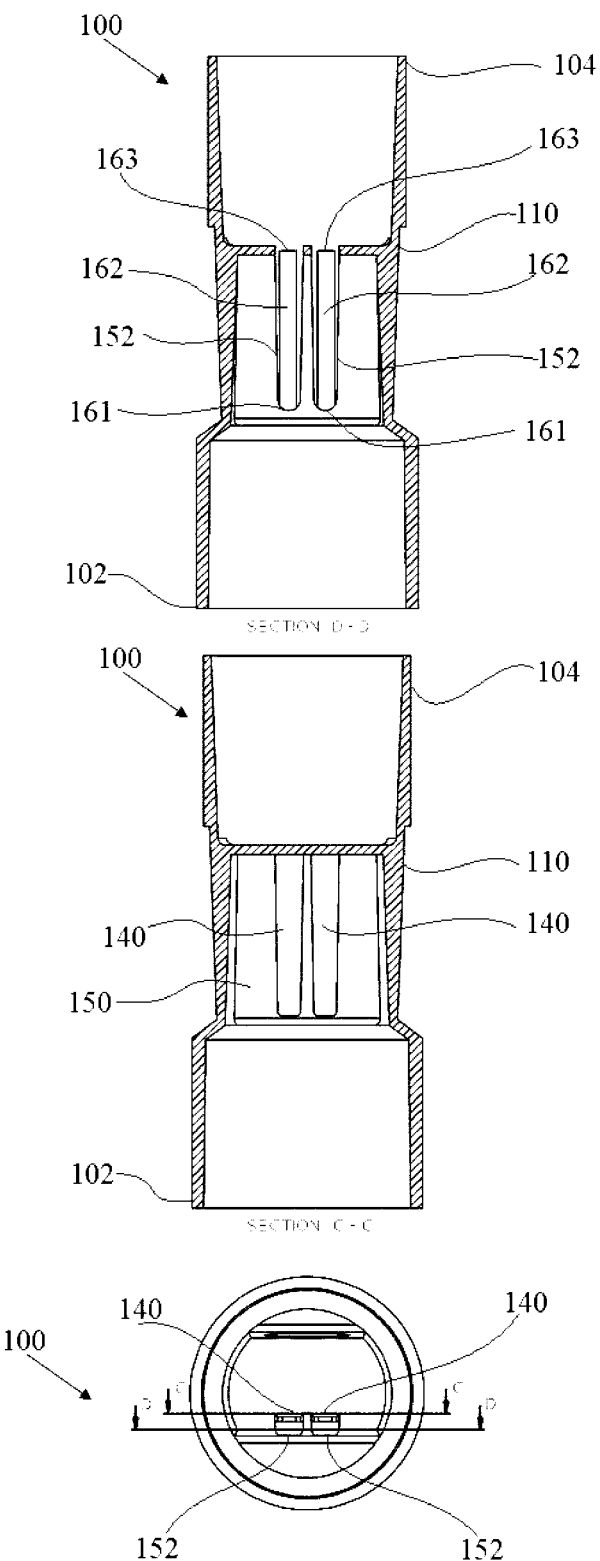
FIG. 10A shows respective cross sectional views and a front view of a delivery device configuration with two reeds, two slots and two eddy generators.
Figure 10B:
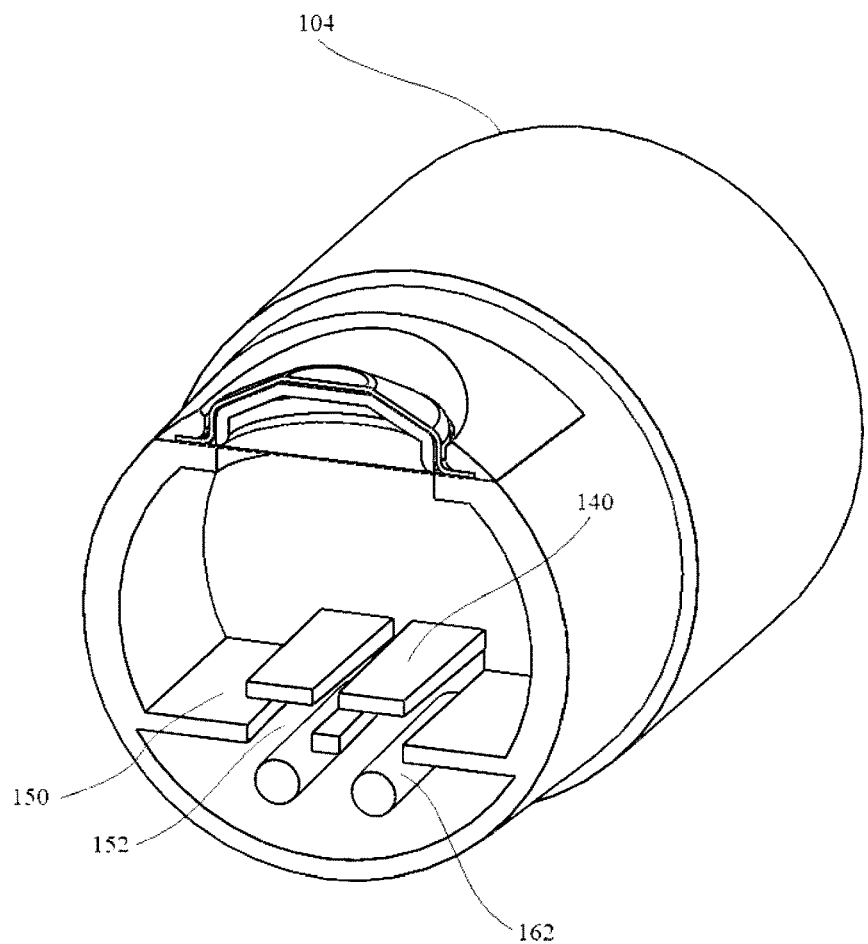
FIG. 10B shows a cross sectional perspective view of the delivery device configuration of FIG. 10A.
Figure 10C:
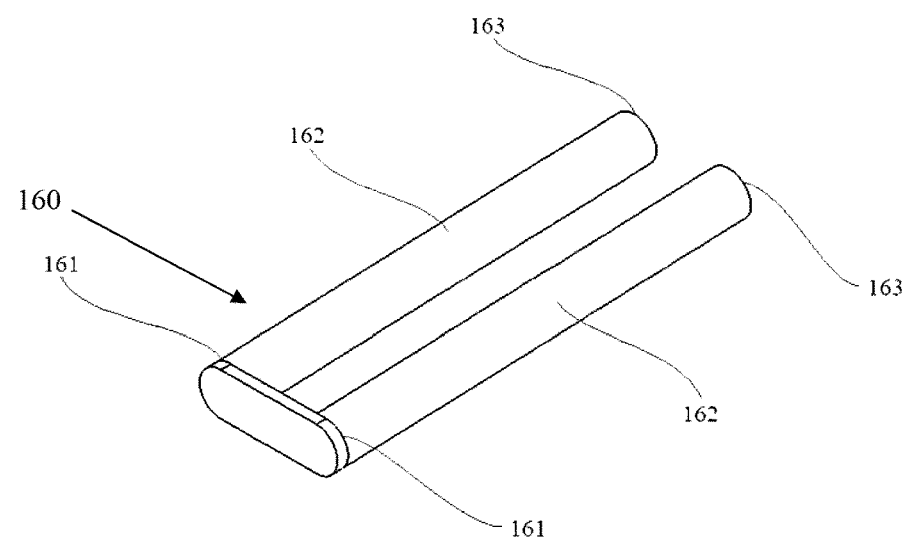
FIG. 10C shows the eddy generator structure of FIGS. 10A.
Figure 11:
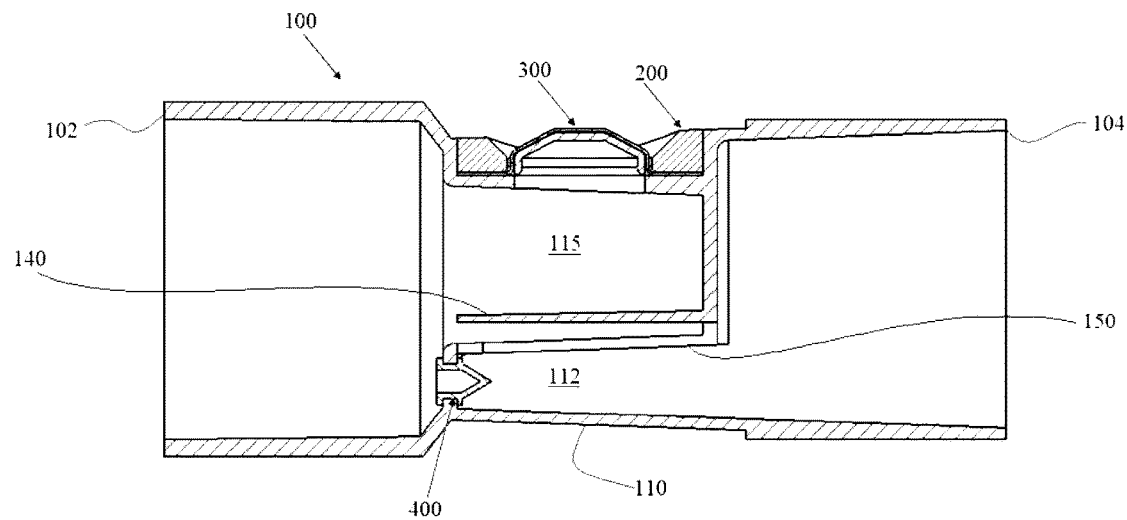
FIG. 11 shows a cross sectional view of an exemplary delivery device with an internal pressure relief valve.
Figure 12:
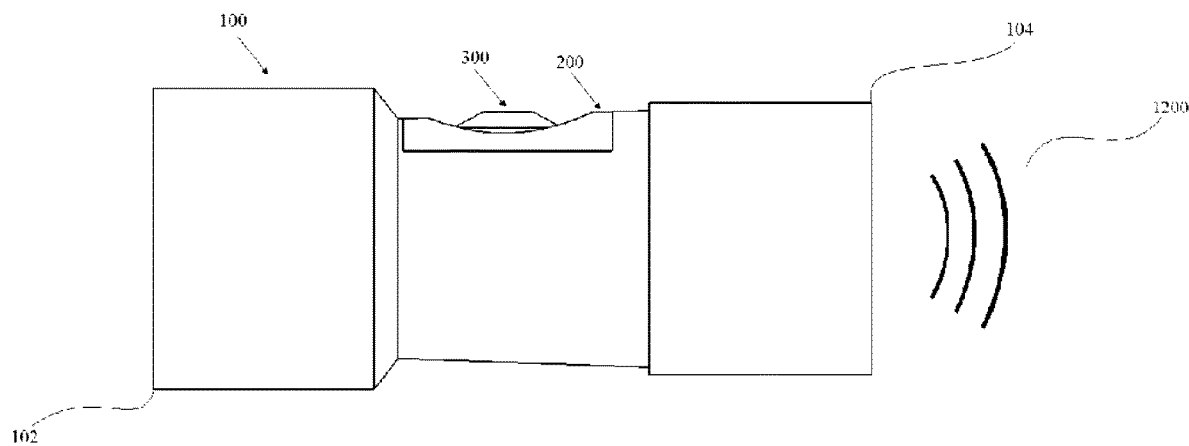
FIG. 12 is a side view of the delivery device of FIG. 1A in operation producing an audible sound, indicating that the device is operating correctly.

As shown in FIGS. 8B, 9B and 10B, the fixed members 162 are disposed directly beneath the deagglomerating surface 150. The fixed members 162 extend lengthwise from a first end 161 to a second end 163 as shown in FIGS. 5B, 8A, 9A and 10A, for example. The fixed members are arranged within the housing so that the bars 162 are each located directly beneath a respective slot 152 of the deagglomerating surface 150 (see FIGS. 9B and 10B for example). In this way, the entrained dry powder flows through the slots 152 and then is interrupted by the fixed members 162. The fixed members 162 such as bars therefore create fluid turbulence and induce the formation of small high energy eddies which further deagglomerate the dry powder by fluid turbulence as previously discussed. The fixed members 162 also increase the gas velocity and encourage the powder to become entrained therein.

After this further deagglomeration, the entrained flow of dry powder that reaches space or region 112 inside the housing 110 downstream of the eddy generator structure 160 will have a refined particle size, such as hereinabove described, suitable for delivery to the airway of the patient to maximise efficacy of the drug delivery. In particular, the particles will be of a size that will allow them to reach the alveoli and thus be absorbed into the bloodstream of a patient.

Referring now to FIG. 15, there is shown a schematic example of a method of delivering a dose of dry powder to a biological subject using a delivery device 100 as described above. The dry powder may comprise any suitable active agent, such as hereinabove described.

The delivery device may, for example, have an exhalation valve attached to the inlet 102 of the device 100 and an endotracheal tube attached to the outlet 104 of the device 100, although without limitation thereto.

At step 1500, the method includes generating a flow of gas between the inlet and outlet of the delivery device 100. This may occur in a preparatory phase to ensure effective flow rates through the device and may be carried on until delivery of the medicament is necessary.

The method then includes at step 1510 causing at least a portion of the dose of dry powder to be released within the housing 110. This may occur by vibration of the cantilever structure 140 to release dry powder located therein or thereon, or by rupturing of the container 300, as hereinabove described in detail.

Finally, at step 1520 the method includes delivering the gas flow including the entrained dry powder to the subject's airway. This may be achieved through a universal mask connected to the outlet 104 of the device 100 which is positioned over the subject's mouth, or with a tracheal or laryngeal airway connected to the outlet 104 of the device and inserted into the subject's mouth, although without limitation thereto. Audible feedback 1200 obtained from the vibrating cantilever structure 140 may be used by the operator to regulate airflow.

In one example, the user may be administering CPR to the patient while using the device 100. After delivery of the medicament, gas flow may continue without need for the dry powder to be replaced and/or, when using an embodiment of the device comprising the container 300, for the container to be removed. When the next delivery of medicament is required, a new delivery device 100 is used and the above steps are repeated. Alternatively, in embodiments, the device 100 may permit multiple doses to be delivered using the same device 100 such as by replacing the container 300 as hereinabove described.

Figure 16:
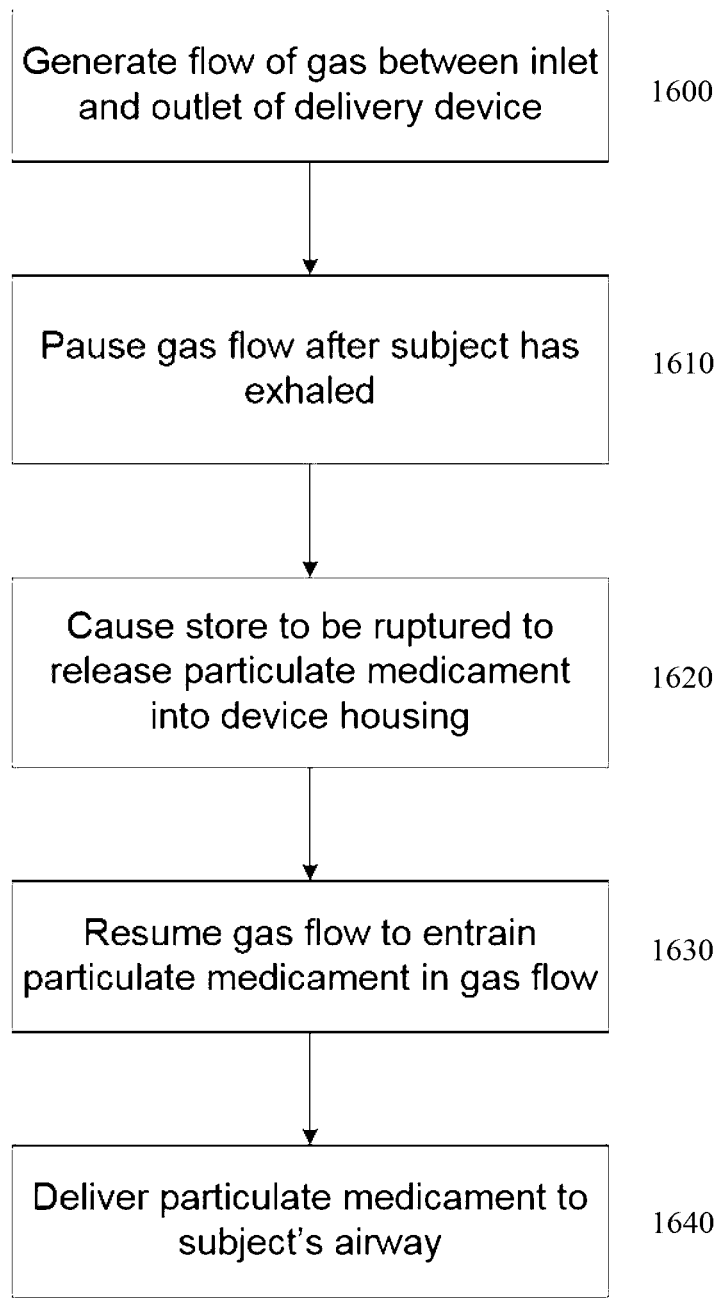
FIG. 16 is a flow chart of an example of another method of delivering a dose of dry powder to a biological subject using a delivery device as described herein.

A more specific example of a method of delivering a dose of dry powder to a biological subject using a delivery device 100 as described above, wherein the delivery device 100 comprises the container 300, shall now be described with reference to the schematic shown in FIG. 16.

At step 1600, the method includes generating a flow of gas between the inlet 102 and outlet 104 as described above to ensure effective flow rates etc. in order to deliver the powder.

After an exhalation is complete, the gas flow is momentarily paused as shown at step 1610. The method then includes at step 1620 causing at least a portion of the store 300 to be ruptured to allow the dose of dry powder to be released into the housing 110 via the opening 106. At step 1630, gas flow is resumed through the device in order to entrain the dry powder in the gas flow. The dry powder is then delivered to the subject's airway at step 1640 as previously described.

A method of administering CPR to a biological subject will now be described. In particular, the method includes performing at least one chest compression on the subject, and supplying at least one medicated breath. In this regard, the medicated breath includes a positive pressure gas in an amount corresponding to an artificial breath, and an entrained dose of dry powder. The dry powder may include any suitable medicament depending upon the subject and their condition, such as any of the medicaments discussed above, and in one example includes microparticles containing adrenaline as the active pharmaceutical ingredient.

Further, it will be appreciated that the amount of gas corresponding to an artificial breath is an amount which is known in the art, and typically is dependent upon the size and nature of the subject. For example, the amount corresponding to an artificial breath for an infant is smaller in volume than for an adult biological subject. In addition, the amount typically also corresponds to an amount of gas supplied during a ventilation breath, also referred to as rescue breath, provided during conventional CPR and hence would be well known to the skilled person.

In particular, this method of administering CPR offers a number of significant advantages.

For example, the medicated breaths enable the subject to be simultaneously ventilated and medicated, thus an operator need not cease chest compressions in order to administer the medicament, and this may significantly improve the subject's prognosis. Furthermore, as the dry powder is delivered while entrained in the positive pressure gas flow, it will rapidly flow through the subject's airways into the alveoli where it is rapidly absorbed into the blood stream, and circulated to the target organ(s).

In instances where the subject has undergone cardiac arrest, performing CPR including supplying medicated breaths provides a mechanism to rapidly deliver adrenaline to the subject's blood stream, via the lungs, and from the blood stream to cardiac tissue. Furthermore, the subject may be simultaneously ventilated and medicated with adrenaline, thus enabling a single operator to perform both functions without having to interrupt the CPR, which in turn increases the subject's chances of survival as well as decreasing the risk of severe disability post-resuscitation.

In addition, a plurality of doses of particulate adrenaline may be administered to the subject via multiple medicated breaths during CPR. In this regard, as one medicated breath typically corresponds to one dose of particulate adrenaline, as more medicated breaths are supplied to the subject's airways, more doses of adrenaline are delivered to the cardiac tissue and thus the subject's prognosis is significantly improved. Hence, the method may include performing the chest compressions and supplying the medicated breaths in any suitable ratio, for example a ratio of any one of 30:2, 30:1, and 60:1, or any other suitable amount as current best practice dictates. It is to be appreciated that the delivery device described herein is for delivering a single dose of dry powder only (i.e. a single-use device). In order to administer multiple doses using this example, another device would typically be used or the device itself may be configured to deliver multiple doses.

It is to be further appreciated that the method may also include one or more non-medicated breaths, for example, supplying positive pressure gas in an amount corresponding to an artificial breath without an entrained dose of dry powder, similar to known ventilation breaths provided during conventional CPR. In this regard, the method of performing CPR may include performing 30 chest compressions, supplying two non-medicated breaths, performing 30 chest compressions, supplying one medicated breath and one non-medicated breath, and repeating the above steps. However, this is not essential and any combination of performing chest compressions, and supplying medicated and non-medicated breaths may be performed.

It is to be noted that the above described device is sufficiently simple and relatively small to be made available in any environment outside of specialised medical centres, such as in the home, ambulance, shopping centres, public buildings, and the like. Thus, by performing this method any subject requiring CPR outside of a hospital or medical centre will have an improved prognosis in terms of return of spontaneous circulation, survival and post-resuscitation quality of life.

Thus, it will be appreciated that the delivery device 100 may be used when performing CPR, or any other type of artificial respiration, on a subject. In this regard, the gas is supplied in amounts corresponding to artificial breaths such that the particulate adrenaline is delivered to the subject when the operator administers the breath to the subject, for example, via the operator exhaling into the inlet 102, or using a BVM in fluid communication with the inlet 102, or similar. The device is designed such that is can be used as a single-use only. Hence the delivery device 100 allows for on-site administration of adrenaline to a subject undergoing cardiac arrest, which in turn improves life expectancy and post-resuscitation outcomes.

It will be appreciated that the simplicity of this delivery device 100 is particularly advantageous for its provision in first aid kits, hand bags, school bags and for travelling, in the home, office, or the like.

In use, an operator simply positions the outlet 104 in fluid communication with a subject's airway, and exhales into the inlet 102 thereby administering the medicament. However, this is not essential and the delivery device 100 may be used in any suitable environment, including with a BVM, mask, mouthpiece, or the like, thus providing a portable and versatile arrangement. Alternatively, the subject may use the delivery device 100 themselves and inhale the medicament by breathing in through the outlet 104.

It will be appreciated that the delivery device 100 may contain any desired medicament, for example, such that an apparatus containing adrenaline may be used for subjects with cardiac dysfunction or anaphylaxis, or an apparatus containing glucose and/or glucagon may be used with the same in the event a subject is hypoglycaemic. Similarly, the device 100 may contain naloxone for use with a drug overdose or phenytoin for use in the event that a subject has a seizure. Thus, various apparatus containing different medicaments may be provided in a kit, such that the operator or subject may select the appropriate apparatus depending upon the subject's condition.

In one example, one or more delivery devices 100 may be provided in a kit, which additionally includes any one or more of a mask, a Bag-Valve-Mask (BVM) (e.g. Ambubag), a resuscitation bag, a defibrillator, different models of the apparatus containing different medicaments or additional apparatus containing the same medicament.

As previously described, the delivery device 100 may also be used with negative pressure gas, such that as gas under negative pressure flows from the inlet 102 to the outlet 104, the dry powder is entrained in the gas flow and delivered to the subject's airway. In particular, the negative pressure gas may be supplied by the subject, and this is particularly suited to situations where the subject is conscious and responsive. For example, a subject suffering anaphylaxis or hypoglycaemia may utilise the delivery device 100 quickly and effectively in order to rapidly administer themselves with one or more doses of adrenaline or glucose/glucagon, respectively, in order to treat their condition and avoid further deterioration.

Furthermore, the administration of adrenaline in this way will result in both local and systemic responses, which will be particularly effective in the case of anaphylaxis where there is swelling in the mouth and throat. In this case, the particulate adrenaline will be administered both directly to the affected swollen tissues in the upper airway, and subsequently to the bloodstream, via the alveoli, to provide a systemic response.

Furthermore, the delivery device 100 is highly portable, such that a subject prone to any one of the above conditions would be able to carry the apparatus with them, for example, in a pocket, handbag, purse, schoolbag, or the like. Additionally, as the delivery device 100 may be used with positive or negative pressure, in the event a subject deteriorates to a state of unresponsiveness, an operator may use the delivery device 100 to administer a dose of dry powder.

In one example, the above described delivery device provides the potential for safe, rapid delivery of a life-saving drug (e.g. adrenaline) without the time delay for arrival of skilled paramedics or the need for putting an intravenous cannula in (small plastic tube that sits in a vein) or pouring drugs into the lungs through an advanced airway or injecting the drug into a metal needle in the bone, which are alternative methods when a cannula cannot be inserted. The device 100 allows rapid delivery of very small particles of adrenaline to be delivered directly to the lungs with each breath.

This rapid delivery of adrenaline to the lungs gets absorbed through the lung tissue to the blood and then the heart and may help during a cardiac arrest to return to normal heart pumping. Early intervention during a cardiac arrest could save more lives and avoid poor recovery from a cardiac arrest which very frequently includes irreversible brain injury. It is exceptionally simple to use and could be applied in schools, sporting and entertainment venues, ambulances and hospitals amongst other areas. The device 100 could be used by a single person such as a bystander, parent, teacher or paramedic to revive a-patient. The rapid delivery device 100 can potentially be used to deliver improved, rapid treatment, and this may translate into better results, to patients throughout the community.

So that the invention may be readily understood and put into effect, the following non-limiting examples are provided.

EXAMPLES

Example 1

Container Design and Operation

Figure 17:
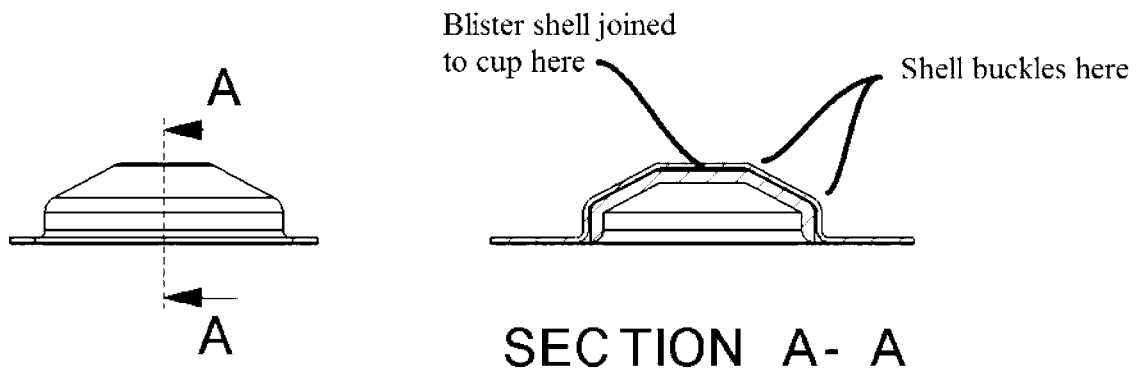
FIG. 17 sets forth particular features of the container of FIG. 4.

With reference to FIG. 17, this example provides further detail in relation to structure and operation of preferred containers as described herein.

It will be appreciated that the blister shell of preferred containers is designed such that the top of the blister preferentially buckles towards the seal (e.g. foil seal). This operation is adapted to facilitate breakage of the seal by the puncturing cup.

It will also be understood that the puncturing cup is preferably secured at the top centre of the blister shell, e.g. by weld or glue.

Example 2

Reed Design and Operation

It has been determined in the context of the invention that delivery device operation is sensitive to flow rate. As set forth herein, the operating range of the device refers to the range of flow rates at which the cantilever structure or reed vibrates.

Figure 18:
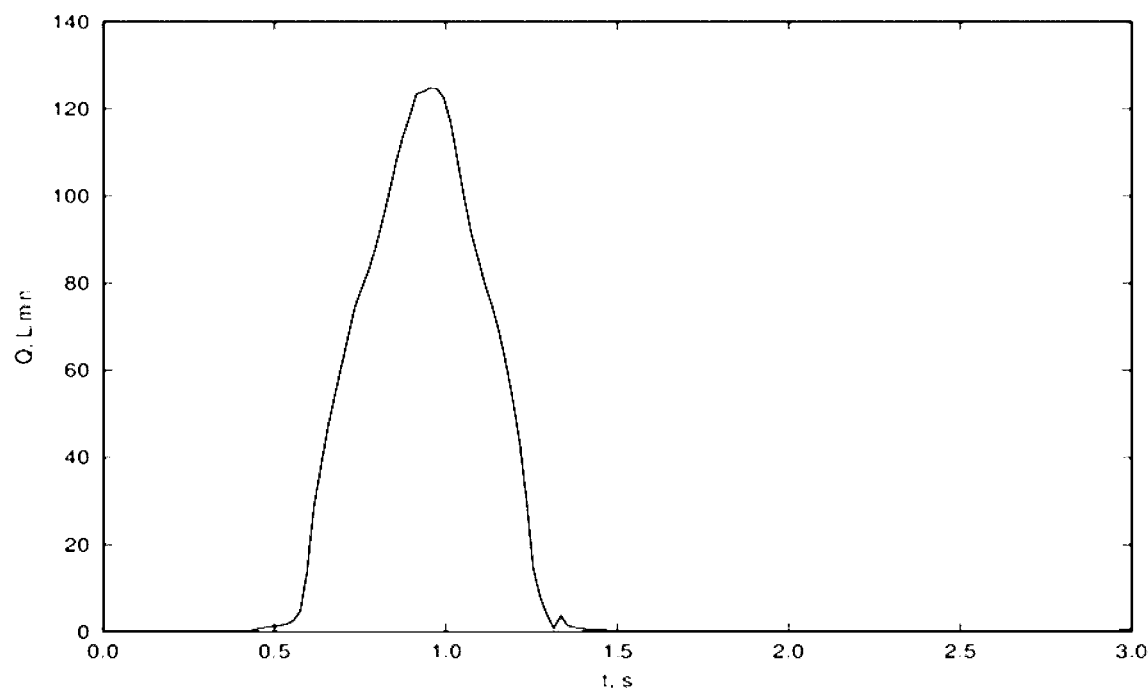
FIG. 18 sets forth data on flow rates provided when manually ventilating an artificial lung.

At least preferred embodiments of the device are adapted to operate for air flow rates similar to those used during ventilation of patients. Peak flow rates for nurses ventilating an artificial lung in a controlled environment using a bag-valve-mask (BVM) were measured to be about 80 L/min. However, in a 'real world' scenario, flow rates seen during ventilation often exceed this range. FIG. 18 shows the flow rates provided by when manually ventilating an artificial lung for one breath for a 'worst-case' condition.

As described herein, the delivery device can have one or more reeds, but preferably one. Two reeds typically requires approximately twice the airflow to operate, and it is preferable that operation begins at a low flow rate such that deagglomeration occurs over the entire duration of the artificial breath.

The reed operating range is dependent on a number of key parameters defined in FIG. 19.

It is particularly preferred that reed tip clearance is between 0.1 mm to 5 mm, even more preferably 0.4 mm to 4 mm. This parameter is critical to controlling the operating range. An increase of 0.1 mm has been found to correlates to a 5-10 L/min higher starting flow rate for this design, as shown in FIG. 20.

If the overlap between the reed and the deagglomerating surface is too high, the force on the reed reduces and so operation is compromised. If the overlap it is too low there is less area available for deagglomeration. Accordingly, it is particularly preferred that the void area to reed area ratio for this design is between 1% and 200%, even more preferably between 20% to 120% of the reed area, with reference to FIG. 21.

The reed length, geometry and material, contribute to determining its natural frequency. With reference to FIG. 22, it is particularly preferred that the reed length is between 1 mm and 100 mm, even more preferably between 5 and 40 mm.

Testing of reed material has determined that it is preferred for the material to demonstrate relatively high specific elastic modulus, that is, elastic modulus divided by density, (e.g. between 1-100 GPa.cm ^3/g) and low damping ratio (e.g. <0.15), for optimum performance. Thus, materials with a high elastic modulus and low density are preferable, such as metals, polymers (including polycarbonate, acrylic, and polystyrene) and composites thereof.

FIG. 23 sets out an assessment of the specific modulus in relation to starting flow rate. The figure also demonstrates that the addition of Talc filler, which increase the damping coefficient of the material (polyurethane), increases the starting flow rate.

A General Purpose Polystyrene (GPPS) prototype reed was found to have an operating range of between 50 to greater than 120 L/min. FIG. 24 shows pressure drop across this device for a range of flow rates. It is intended that further optimisation of the reed geometry and material will be conducted such that a larger operating range is achieved, preferably between 20 to 140 L/min.

Additionally, the operating range for a device with one reed was compared with the operating range for a device with two reeds (see Table 1). It is to be noted that the reeds used for this assessment were different as compared to GPPS prototype, being formed of plastic, sourced commercially, and of a type conventionally used in 'party horn' -type blower devices.

The two-reed device required twice the flow rate to begin operation, which may be the result of it having effectively double the void area as compared to the single reed device. Thus for the device to operate over the largest range of flow rates possible, a one-reed device can be particularly advantageous.

TABLE 1

Comparison of operating range for one- and two-reed devices

| | Operating range (L/min) |
|---|---|
| One-reed device | 31-73+ |
| Two-reed device | 68.67-73+ |

Example 3

Pressure Release Valve

An assessment of the pressure drop across the delivery device as described herein (in bold), as compared to that seen in known commercial inhalers (as described in Kruger P, Ehrlein, Zier M, Greguletz R. *Inspiratory flow resistance of marketed dry powder inhalers*. Munich, Germany: Oral presentation at the European Respiratory Society Annual Meeting, Sep. 6-10, 2014, proceedings), is provided in FIG. 25.

It has been found that at some high flow rates, the reed may seal against the deagglomerating surface, which can result in a sudden, high back pressure. To accommodate this, a pressure relief valve (FIG. 11) may be added to relieve pressure should this occur.

Example 4

Acoustic Isolator

During 'real world' scenarios, the delivery device may be used with a variety of advanced airways such as a Laryngeal

Figure 26:
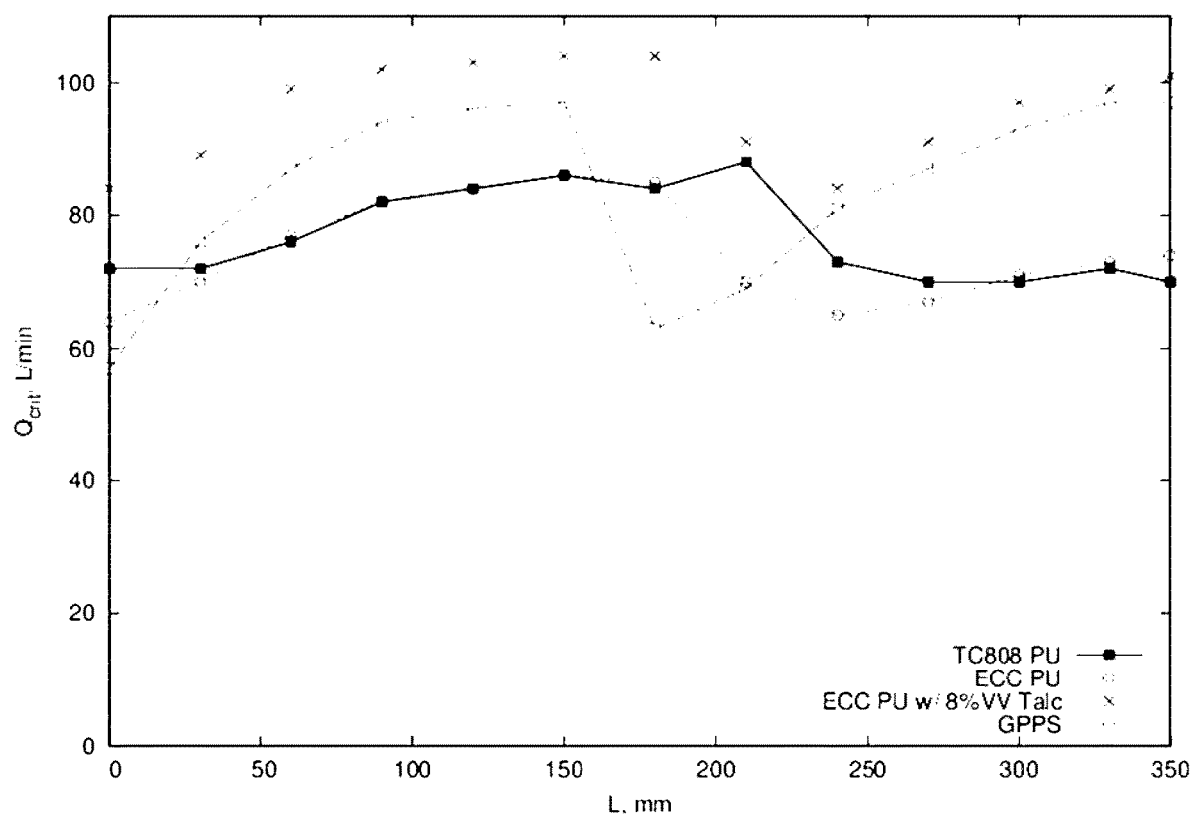
FIG. 26 sets forth data on starting flow rate when embodiments of the delivery device are used with advanced airways comprising various lengths of uniform tube.

Mask Airway (LMA), Endotracheal Tube (ETT) and King Laryngeal Tube (King LT). It has been determined that if the delivery device outlet is connected to a tube, such as in this context, the acoustics of the device can change. This can result in a marked change in starting flow rate, as shown in FIG. 26. Furthermore, after testing with a uniform tube (as set out in FIG. 26) the GPPS prototype was tested using: ETT sizes 7-10; King LT sizes 4-5; LMA sizes 3-5 (FIG. 27).

Figure 27:
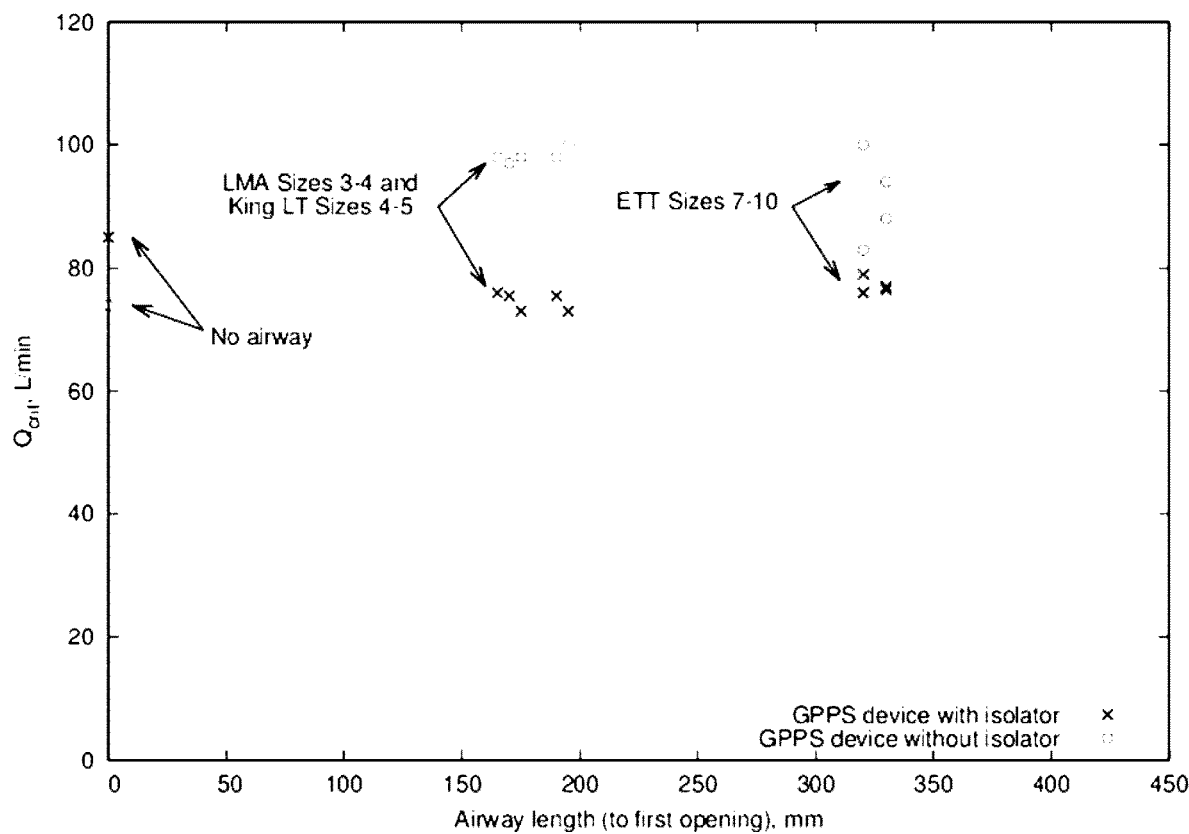
FIG. 27 sets forth data on starting flow rate when embodiments of the delivery device with and without acoustic isolators are used with various advanced airways.

As seen in FIG. 27, it was determined that the addition of an acoustic isolator such as depicted in FIG. 13 can be highly beneficial in relation to achieving a suitable operating flow rate when the delivery device is used in conjunction with advanced airways. Values shown for the respective airway-device combinations are flow rates at which the device began operating. In some cases, such as the LMA sizes 3-4 and King LT sizes 4-5, the device did not commence operating, and instead the reed immediately sealed. In these cases, the sealing flow rates are shown.

Without the acoustic isolator, the device started operating at different flow rates in this context, depending on airway, or did not operate at all. With the addition of the acoustic isolator, the starting flow rate was nearly constant regardless of the airway used. By way of elaboration, the delivery device was unable to operate without the acoustic isolator when using LMA sizes 3-5 or King LT sizes 4-5. Thus the acoustic isolator can assist with allowing the device to operate independently of an airway that is attached.

Example 5

Particle Deagglomeration

Deagglomeration of dry powder by the delivery device was assessed using both Mannitol and Adrenaline.

Figure 28:
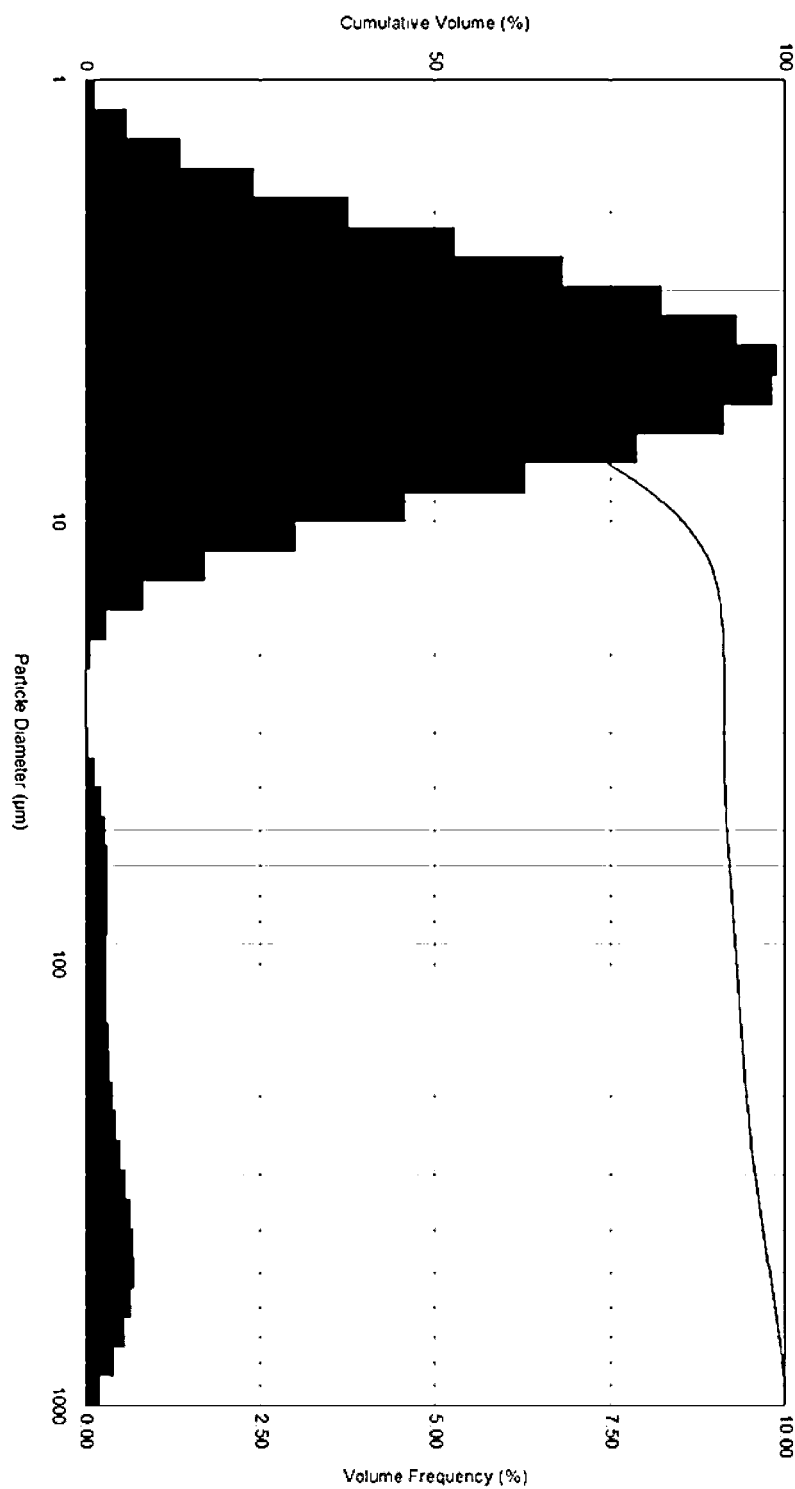
FIG. 28 sets forth data on particle size distribution of emitted dose of Mannitol using an embodiment of the delivery device comprising a container for storing dry powder.
Figure 29:
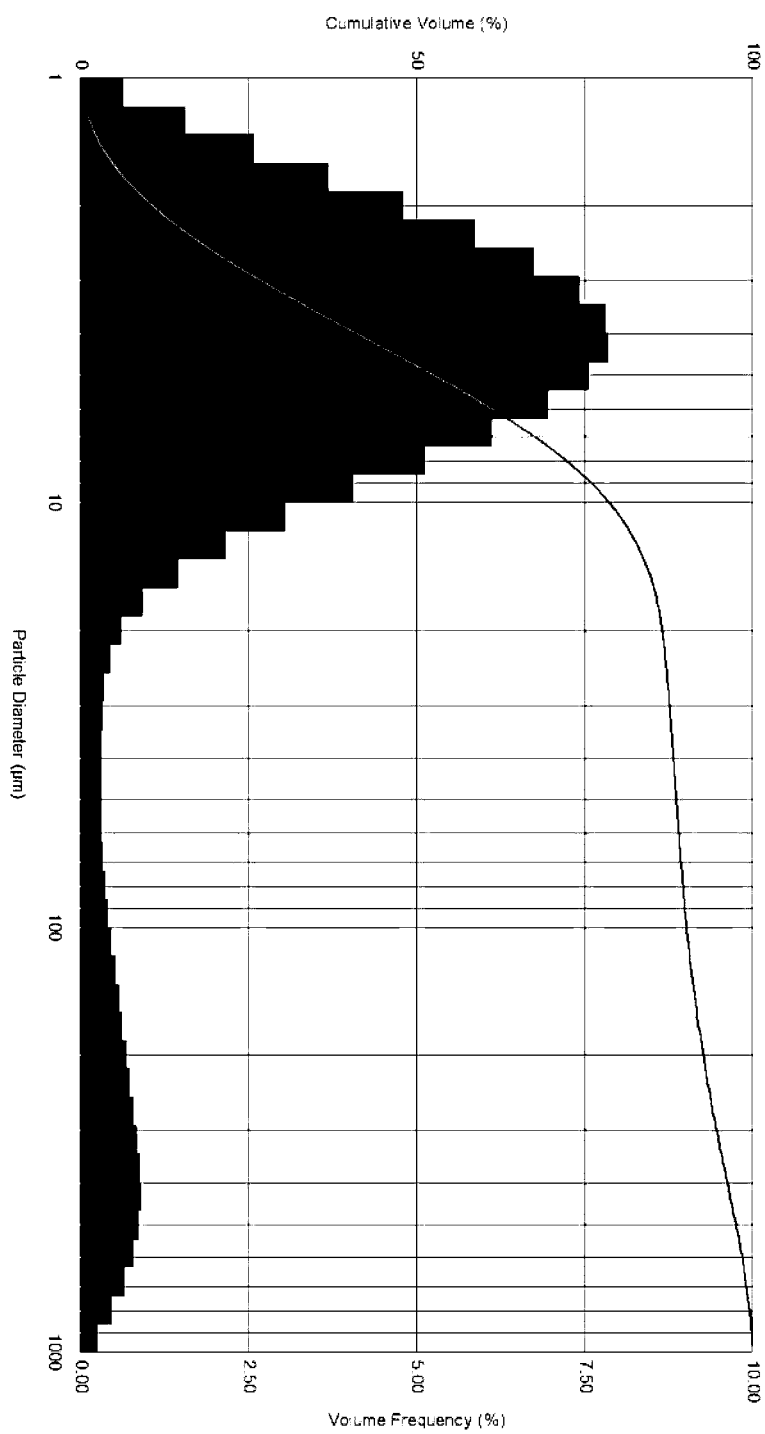
FIG. 29 sets forth data on particle size distribution of emitted dose of Adrenaline using an embodiment of the delivery device comprising a container for storing dry powder.

The original particle size distribution of these dry powders was similar, and within the inhalable range. During storage, however, the particles agglomerated into aggregates, which then changed the particle size distribution. The performance of the delivery device can be measured by how closely the particle size distribution of the emitted powder approaches the original distribution. Particle size distributions of the emitted dose (emitted dose=75.3-86.1% for Mannitol; 72.4-92.0% for Adrenaline) are shown in FIG. 28 for Mannitol and FIG. 29 for Adrenaline.

About 50% of the Mannitol was deagglomerated to the typical inhalable range, whereas about 35% of the Adrenaline was deagglomerated to the typical inhalable range. A summary of these results is shown in Table 2 below.

TABLE 2

Performance of device for Mannitol and Adrenaline (N = 8, 68% CI)

| | Fine Particle Fraction < 5 um (%) |
|---|---|
| Mannitol | 48.0-60.9 |
| Adrenaline | 30.4-37.1 |

Figure 30:
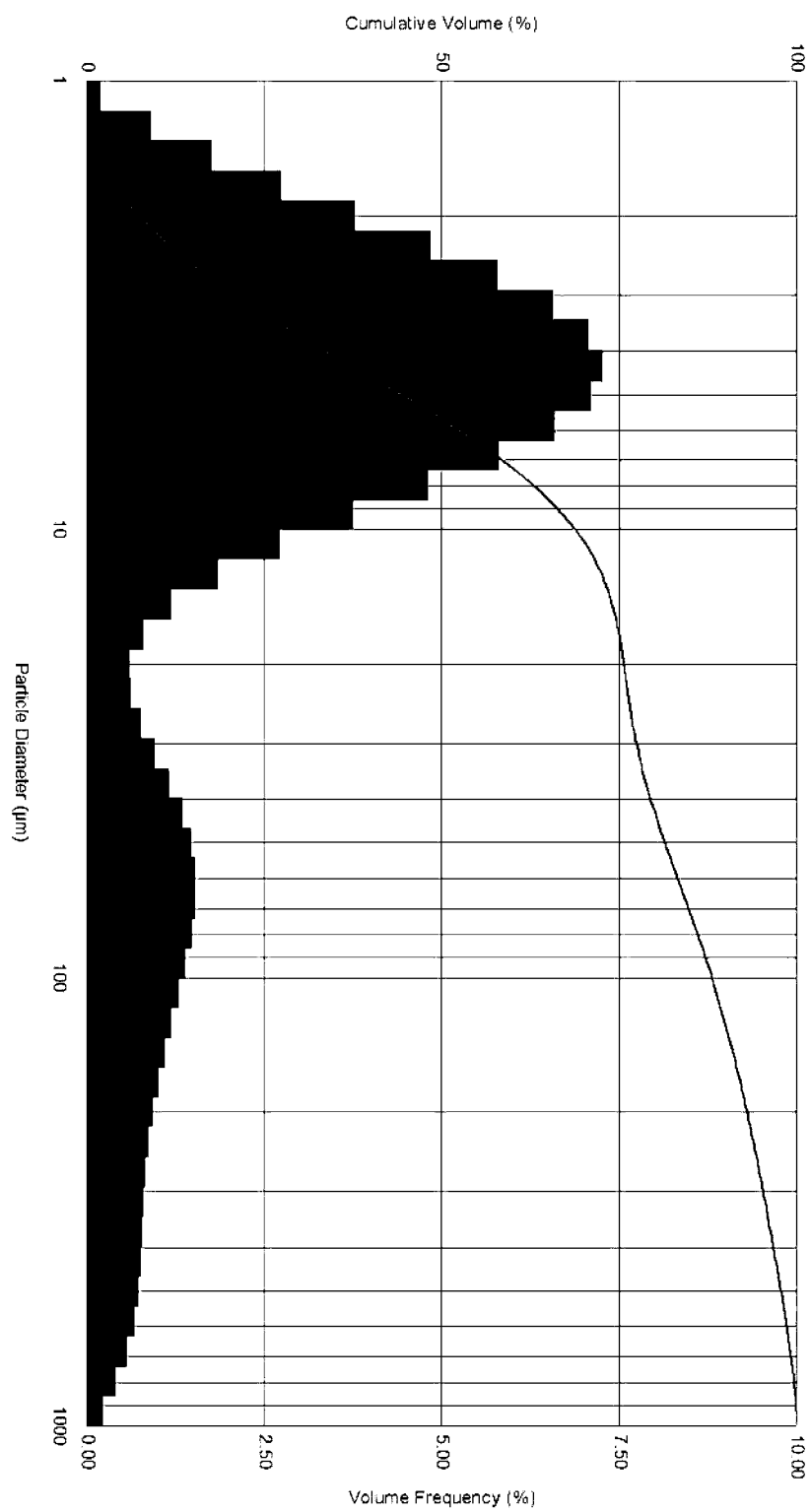
FIG. 30 sets forth data on particulate size distribution of emitted dose of Mannitol using a device as used for FIG. 28, but with the reed removed.

Furthermore, to confirm the importance of the reed of device for delivery, two devices, one with a reed and without a reed, were tested using Mannitol under the same flow conditions. A sample test result for the device without a reed is shown in FIG. 30 for contrast to a device with a reed shown in FIG. 28.

The device with a reed resulted in a FPF of about 43% whereas a device without a reed resulted in a FPF of about 31% (see Table 3). A two sample Student-T test on these results (for unequal variances) showed a p-value of greater than 0.999. Thus the null hypothesis that the reed had no effect was rejected and the presence of a reed has a statistically significant effect on the device performance.

TABLE 3

Performance for device with and without reed (N = 10, 68% CI)

| | Fine Particle Fraction < 5 um (%) |
|---|---|
| Mannitol, with reed | 38.9-47.4 |
| Mannitol, without reed | 26.8-35.1 |

Figure 31:
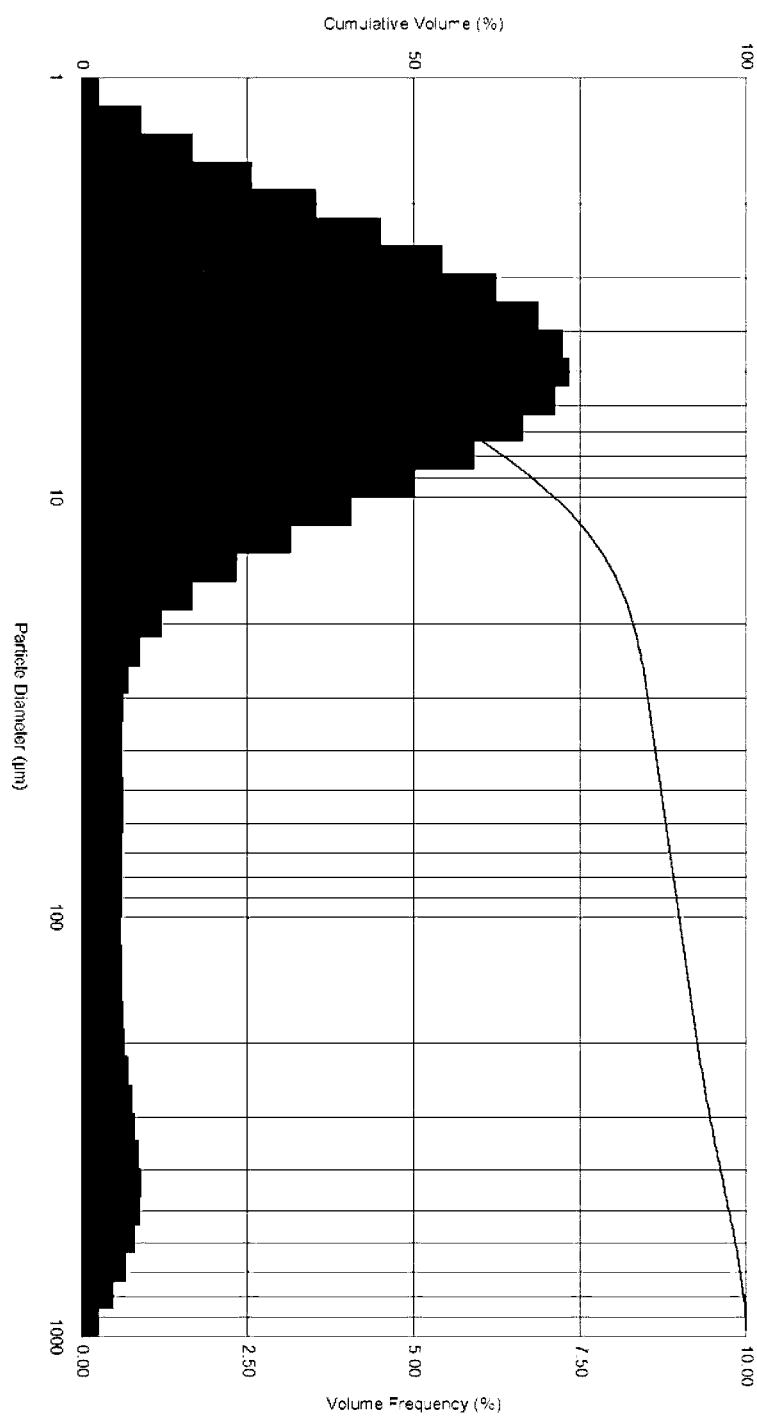
FIG. 31 sets forth data on particle size distribution of emitted dose of Mannitol using an embodiment of the delivery device that stores dry powder on a corrugated reed.

An embodiment of the device that stored Mannitol on a corrugated reed was also compared to the embodiment of the device that stored and dispensed Mannitol from a blister. A sample test result for a corrugated reed is shown in FIG. 31 for comparison to the device with a blister shown in FIG. 29.

The device that dispensed Mannitol from a blister had a FPF of about 43% and device that dispensed Mannitol from the reed had a FPF of about 44% (see Table 4). A two sample Student-T test on these results (for unequal variances) showed a p-value of less than 0.9. Thus, the null hypothesis that dispensing Mannitol from a reed and dispensing Mannitol from a blister have equivalent performance is accepted and there is no significant performance difference between the devices.

TABLE 4

Comparison of performance of devices where powder is stored in a blister, and powder is stored in a corrugated reed (68% CI)

| | Fine Particle Fraction < 5 um (%) |
|---|---|
| Mannitol dispensed from blister (N = 10) | 38.9-47.4 |
| Mannitol dispensed from reed (N = 5) | 40.6-48.2 |

Example 6

Ex Vivo Testing for Dose Finding

Ex vivo testing is to be performed as part of a dose finding study. The aim of the dosing study is to find the loaded dose of powdered adrenaline that is equivalent to 1 mg IV adrenaline. This will involve explanting of sheep lungs into an ex-vivo rig. The lungs will be kept alive on life support. The lungs will be administered different doses of powdered adrenaline, selected randomly, and compared to 1 mg IV adrenaline and a control. The blood concentration of adrenaline will be taken at 1-minute intervals post-administration to allow for comparison.

It is anticipated that these studies will result in an estimate of the loaded dose required for a therapeutic dose equivalent to 1 mg IV adrenaline.

Example 7

Andersen Cascade Impactor Tests

Andersen Cascade Impactor testing is to be performed to assess and optimise Fine Particle Dose achieved by the delivery device described herein. The methodology that will be used is the US Pharmacopea standard testing method for dry powder inhalers. FPD of the device will be compared to a known "gold standard" dry powder inhaler.

It is anticipated that these studies will assist in further optimisation of the device by quantifying performance.

Example 8

Animal Trials

Efficacy of embodiments of the device of the invention for delivery of various agents is to be further explored using animal models. The methodology that will be used is an animal study showing the effect of pulmonary delivery of adrenaline on brain oxygen levels in at least two different animal types that have undergone cardiac arrest. Pulmonary adrenaline will be delivered using the device, and compared to 1 mg IV injection and a sham and a control.

It is anticipated that these studies will provide pre-clinical data that will demonstrate the benefit of the device, and facilitate proceeding to clinical trials.

The preceding description of various embodiments of the present invention is provided for purposes of description to one of ordinary skill in the related art. It is not intended to be exhaustive or to limit the invention to a single disclosed embodiment.

Numerous alternatives and variations to the present invention will be apparent to those skilled in the art of the above teaching. Accordingly, while some alternative embodiments have been discussed specifically, other embodiments will be apparent or relatively easily developed by those of ordinary skill in the art. The invention is intended to embrace all alternatives, modifications, and variations of the present invention that have been discussed herein, and other embodiments that fall within the spirit and scope of the above described invention. It will be appreciated that features from different examples above may be used interchangeably where appropriate.

The claims defining the invention are as follows:

1. A delivery device for use in administering a dry powder to a biological subject's airway, the device comprising:
    a) a housing having an inlet in fluid communication with an outlet for delivering a flow of gas to the subject's airway; and
    b) one or more cantilever structures located within the housing,
    wherein the device comprises a container for storing a dose of the dry powder, wherein the container is engaged or engageable with the housing so as to cover an opening in the housing located part way between the inlet and the outlet;
    wherein the container is configured to be at least partially rupturable to allow the dose of the dry powder to be released into the housing via the opening, such that at least a portion of the dry powder dose is located in proximity to the one or more cantilever structures;
    wherein vibration of the one or more cantilever structures is configured to facilitate entry of the dose of the dry powder into the flow of gas, such that the dry powder can be delivered by the flow of gas through the outlet to the subject's airway.

2. The delivery device of claim 1, wherein the device is configured such that gas flow through the housing forces the one or more cantilever structures to vibrate.

3. The delivery device of claim 1, wherein the one or more cantilever structures are reeds.

4. The delivery device of claim 1, wherein the device further comprises a deagglomerating surface, wherein the one or more cantilever structures are configured to vibrate against, or in close proximity to, the deagglomerating surface.

5. The delivery device of claim 1, wherein the housing of the device comprises a filter in the form of one or more openings, for allowing particles of the dry powder of a maximum size to be delivered to the subject's airway.

6. The delivery device of claim 1, wherein the vibration of the one or more cantilever structures is configured to occur with gas flow over a range of gas flow rates commensurate with those provided by one or more expected sources of gas supply.

7. The delivery device of claim 4, wherein the housing further comprises one or more eddy generating structures disposed downstream of the deagglomerating surface, wherein the one or more eddy generating structure are configured to generate eddies that promote deagglomeration of the entrained dry powder.

8. The delivery device of claim 7, wherein the one or more eddy generating structures comprise an array of fixed, spaced apart and/or parallel, elongate members forming a staggered arrangement with the deagglomerating surface.

9. The delivery device of claim 1, wherein the device comprises at least one of:
    a) a one-way valve;
    b) an exhalation valve; and,
    c) an adaptor that provides a mechanism to attach a valve,
    for preventing reverse flow of the gas through the inlet.

10. The delivery device of claim 1, wherein the device comprises an acoustic isolator.

11. A method of delivering a dose of dry powder to a biological subject using a delivery device, the delivery device comprising a housing having an inlet in fluid communication with an outlet and one or more cantilever structures located within the housing, the method including the steps of:
    a) generating a flow of gas between the inlet and outlet;
    b) vibrating the one or more cantilever structures to facilitate entry of the dry powder into the flow of gas; and
    c) delivering dry powder entrained in the gas flow to the subject's airway,
    wherein the step of generating the flow of gas between the inlet and the outlet facilitates vibration of the one or more cantilever structures; and
    wherein the dry powder is stored within a container of the device engaged with the housing so as to cover an opening in the housing located part way between the inlet and the outlet, and the method includes the step of at least partially rupturing the container to allow the dose of dry powder to be released into the housing via the opening, whereby at least a portion of the dry powder engages with the one or more cantilever structures.

12. The method of claim 11, wherein delivering the dry powder into the subject's lungs does not require the subject to inhale.

* * * * *